(12) United States Patent
Sekar et al.

(10) Patent No.: US 7,807,791 B2
(45) Date of Patent: Oct. 5, 2010

(54) ANTIBODIES IMMUNOREACTIVE WITH MUTANT 5-ENOLPYRUVLSHIKIMATE-3-PHOSPHATE SYNTHASE

(75) Inventors: Vaithilingam Sekar, Ames, IA (US); Bruce Held, Ames, IA (US); Kyu Chung, Granger, IN (US); Paul F. Russell, Jr., Portage, MI (US)

(73) Assignee: MS Technologies LLC, West Point, IA (US)

( * ) Notice: Subject to any disclaimer, the term of this patent is extended or adjusted under 35 U.S.C. 154(b) by 2 days.

(21) Appl. No.: 12/212,048

(22) Filed: Sep. 17, 2008

(65) Prior Publication Data

US 2009/0220999 A1    Sep. 3, 2009

Related U.S. Application Data

(60) Provisional application No. 61/033,063, filed on Mar. 3, 2008.

(51) Int. Cl.
*C07K 16/00* (2006.01)
*C12P 21/06* (2006.01)
*G01N 33/53* (2006.01)

(52) U.S. Cl. ............... 530/387.1; 530/388.1; 530/388.5
(58) Field of Classification Search ........................ None
See application file for complete search history.

(56) References Cited

U.S. PATENT DOCUMENTS

| | | |
|---|---|---|
| 4,535,060 A | 8/1985 | Comai |
| 4,769,061 A | 9/1988 | Comai |
| 5,094,945 A | 3/1992 | Comai |
| 5,310,667 A | 5/1994 | Eichholtz |
| 5,866,775 A | 2/1999 | Eichholtz |
| 6,040,497 A | 3/2000 | Spencer |
| 6,225,114 B1 | 5/2001 | Eichholtz |
| 6,248,876 B1 | 6/2001 | Barry |
| 6,338,961 B1 | 1/2002 | Derose |
| 6,566,587 B1 | 5/2003 | Lebrun |
| 6,927,319 B2 | 8/2005 | Davis |
| 7,045,684 B1 | 5/2006 | Held |
| 2003/0022253 A1 | 1/2003 | Moskal |
| 2007/0295251 A1 | 12/2007 | Heinrichs |
| 2007/0300323 A1 | 12/2007 | Hershey |

FOREIGN PATENT DOCUMENTS

WO    WO 01/98523 A2 * 12/2001

OTHER PUBLICATIONS

Abbas et al. Cellular and Molecular Immunology 4th edition, 2000, p. 55 and 477.*
Houghten et al. (New Approaches to Immunization, Vaccines 86, Cold Spring Harbor Laboratory, p. 21-25, 1986.*
Colman et al. Research in Immunology 145: 33-36, 1994.*
GenBank Accession No. X63374 "Z. mays mRNA for EPSP-synthase" Apr. 18, 2005.

* cited by examiner

*Primary Examiner*—Mark Navarro
(74) *Attorney, Agent, or Firm*—Patricia A. Sweeney

(57) ABSTRACT

Antibodies immunoreactive to double mutant EPSPS are provided, and in an embodiment the double mutant EPSPS is one in which the wild-type EPSPS is substituted at residue 102 with isoleucine and at residue 106 with serine. Also provided are hybridomas producing the antibodies, as well as methods of making and using the antibodies.

19 Claims, 6 Drawing Sheets

Figure 1

GenBank Accession # : X63374 line 1; amino acid line 2

(atg)

```
        gcgggtgccgaggagatcgtgctgcagcccatcaaggagatc
        A₁  G  A  E  E  I  V  L  Q  P  I  K  E  I
tccggcaccgtcaagctgccggggtccaagtcgctttccaaccgg
 S  G  T  V  K  L  P  G  S  K  S  L  S  N  R
atcctcctactcgccgccctgtccgaggggacaacagtggttgat
 I  L  L  L  A  A  L  S  E  G  T  T  V  V  D
aacctgctgaacagtgaggatgtccactacatgctcggggccttg
 N  L  L  N  S  E  D  V  H  Y  M  L  G  A  L
aggactcttggtctctctgtcgaagcggacaaagctgccaaaaga
 R  T  L  G  L  S  V  E  A  D  K  A  A  K  R
gctgtagttgttggctgtggtggaaagttcccagttgaggatgct
 A  V  V  V  G  C  G  G  K  F  P  V  E  D  A
aaagaggaagtgcagctcttcttggggaatgctggaactgcaatg
 K  E  E  V  Q  L  F  L  G  N  A  G  T₁₀₂ A  M
cggccattgacagcagctgttactgctgctggtggaaatgcaact
 R  P₁₀₆ L  T  A  A  V  T  A  A  G  G  N  A  T
tacgtgcttgatggagtaccaagaatgagggagagaccattggc
 Y  V  L  D  G  V  P  R  M  R  E  R  P  I  G
gacttggttgtcggattgaagcagcttggtgcagatgttgattgt
 D  L  V  V  G  L  K  Q  L  G  A  D  V  D  C
ttccttggcactgactgcccacctgttcgtgtcaatggaatcgga
 F  L  G  T  D  C  P  P  V  R  V  N  G  I  G
gggctacctggtggcaaggtcaagctgtctggctccatcagcagt
 G  L  P  G  G  K  V  K  L  S  G  S  I  S  S
cagtacttgagtgccttgctgatggctgctccttttggctcttggg
 Q  Y  L  S  A  L  L  M  A  A  P  L  A  L  G
gatgtggagattgaaatcattgataaattaatctccattccgtac
 D  V  E  I  E  I  I  D  K  L  I  S  I  P  Y
gtcgaaatgacattgagattgatggagcgttttggtgtgaaagca
 V  E  M  T  L  R  L  M  E  R  F  G  V  K  A
gagcattctgatagctgggacagattctacattaagggaggtcaa
 E  H  S  D  S  W  D  R  F  Y  I  K  G  G  Q
aaatacaagtcccctaaaaatgcctatgttgaaggtgatgcctca
 K  Y  K  S  P  K  N  A  Y  V  E  G  D  A  S
agcgcaagctatttcttggctggtgctgcaattactggagggact
 S  A  S  Y  F  L  A  G  A  A  I  T  G  G  T
gtgactgtggaaggttgtggcaccaccagtttgcagggtgatgtg
 V  T  V  E  G  C  G  T  T  S  L  Q  G  D  V
aagtttgctgaggtactggagatgatgggagcgaaggttacatgg
 K  F  A  E  V  L  E  M  M  G  A  K  V  T  W
accgagactagcgtaactgttactggcccaccgcgggagccattt
 T  E  T  S  V  T  V  T  G  P  P  R  E  P  F
ggggaggaaacacctcaaggcgattgatgtcaacatgaacaagatg
 G  R  K  H  L  K  A  I  D  V  N  M  N  K  M
cctgatgtcgccatgactcttgctgtggttgccctctttgccgat
 P  D  V  A  M  T  L  A  V  V  A  L  F  A  D
ggcccgacagccatcagagacgtggcttcctggagagtaaaggag
 G  P  T  A  I  R  D  V  A  S  W  R  V  K  E
accgagaggatggttgcgatccggacggagctaaccaagctggga
 T  E  R  M  V  A  I  R  T  E  L  T  K  L  G
gcatctgttgaggaagggccggactactgcatcatcacgccgccg
 A  S  V  E  E  G  P  D  Y  C  I  I  T  P  P
gagaagctgaacgtgacggcgatcgacacgtacgacgaccacagg
 E  K  L  N  V  T  A  I  D  T  Y  D  D  H  R
atggccatggccttctcccttgccgcctgtgccgaggtccccgtc
 M  A  M  A  F  S  L  A  A  C  A  E  V  P  V
accatccgggaccctgggtgcacccggaagaccttccccgactac
 T  I  R  D  P  G  C  T  R  K  T  F  P  D  Y
ttcgatgtgctgagcactttcgtcaagaattaa
 F  D  V  L  S  T  F  V  K  N₄₄₄*
```

Figure 2A

```
atcgattgca accttcaaat tctcttcgat cttccttcca aattcatcta atatttcatc      60
ctcggcaagg aaatcttcta acgtgtaaac ttcactggga tccaactcga aaggatcaaa     120
ctctccctct ggttcgtttg acattgtgga tggagtgact aacctgctaa cacccctgcaa    180
caatttatac aggagcatat cctcatgcac acgcaaaact gatgttgtcc acaagacacg     240
cacaggacac gcacaggaca cgcaaacagt ttcagactca tgcacacgca catcagtttc     300
agactcaggc acacgcacat caaatcacct tcgcttgtcg atgagtcgca gccgcatcgt     360
acaatggcga ttttaccgac gataaggcat gggagcacga gccgtcgccg tcgccttgcg     420
agacgacggg agcgatctct cccttcattt aatctcttcc acgtcaggtt attttgctga     480
gatggcagta tacagacggc aaagttaatg ccgttgtaca tgcccttaga ctcttccgtc     540
accaactcac ttagattttt acaacggaac ataaggttcg cttgcagact tacatataag     600
gtatagttgc ataataatcg ccttatgctg tacattgcga cacccgtaaa tattcgatga     660
aatattagta cacaatatta aataagaacg aacaatacat atattatcat tgatcttagt     720
atctccttt  gctcctcgta gaacaattct gtgtaaatta tgcgtaaaat tcgaggacca     780
aaacattggc tagaaaaata cctaaaatca gttttgcaat tgtttctgat tttcctcata    840
ttttcttgct tataaagttt tccaaaagta ccattttgga tgaaaaaacg gaaaacaacg    900
ctggtctact tgtaaatttg gtagtgacat ttgggaccgt ctagacacga cctaaaaata    960
gtagtctaaa acatagtctg acacgatgcc ttaaaaatag acgacaaagc acaacacgat   1020
tagatgtgtc gtgttttgac cgacacgaca caaagtaagg cacgatttaa aacccaataa   1080
ataatatttt aatggttatt ttatgttcca ataattttca tctcttcaaa aaaatgttat   1140
agaaatcatt gatacttagt tgaatatcct aacacaatat atatatatat attaatatat   1200
atatatatca attttaagtc actttgctag acatagtaat atattttaaa tattttctct   1260
ttcttgtata tttttaaaat acacatcagt ttttatatgt gtcgtgcttg aaccgacacg   1320
atataatcat cggttcgccg tacttctaga tcatgatgtt cctaggtttt aatattaaga   1380
gacggtctat attaactcaa aactatttcg tgaaaggcta actcgaaaaa aaaatgaatg   1440
taatcacggc ccgtcctgga ttcgagattc taacgtttca ttcgtgtcca gtgtgcacac   1500
ttgtggaaaa ggaagacgaa gaaaaaaacc aacaactaac tccggcccgc cggatgcgcc   1560
cacctacttc cccctcgccc ctctcatggt ctctctcgcg cccagatctg ctactagacg   1620
gcaccgctgc agcgcgtcgt gtcgcggggg ttggtggcag cagcgagag  cttgccgttc   1680
ctctctctca gttgtcaggt cctaggctca cctcaccggc tcccagcccg cttctatttc   1740
ttcctccccg accccgtgca ggtggcagtc cagtccacgc caccaaccgc gaggcgaacc   1800
aaaccaaccc actctcccca accccgcgcg cccaggccgc ccgccctacc aaccatcggc   1860
gtcggcaatg gcggccatgg cgaccaaggc cgccgcgggc accgtgtcgc tggacctcgc   1920
cgcgccgtcg cgccgccacc accgcccgag ctcggcgcgc ccgcccgccc gccccgccgt   1980
ccgcgggctg cgggcgcctg ggcgccgcgt gatcgccgcg ccgccggcgg cggcagcggc   2040
ggcggcggtg caggcgggtg ccgaggagat cgtgctgcag cccatcaagg agatctccgg   2100
caccgtcaag ctgccggggt ccaagtcgct ttccaaccgg atcctcctgc tcgccgccct   2160
gtccgaggtg agcgattttg gtgcttgctg cgctgccctg tctcactgct acctaaatgt   2220
tttgcctgtc gaataccatg gattctcggt gtaatccatc tcacgatcag atgcaccgca   2280
tgtcgcatgc ctagctctct ctaatttgtc tagtagtttg tatacggatt aatattgata   2340
aatcggtacc gcaaaagcta ggtgtaaata aacactagaa aattggatgt tcccctatcg   2400
gcctgtactc ggctactcgt tcttgtgatg catgctgtc  tcttcttggt gtttggtgaa   2460
caaccttatg aaatttgggc gcaaagaact cgccctcaag ggttgatctt atgccatcgt   2520
catgataaac agtggagcac ggacgatcct ttacgttgtt tttaacaaac tttgtcagaa   2580
aactagcatc attaacttct taatgacgat ttcacaacaa aaaaggtaa  cctcgctact   2640
aacataacaa aatacttgtt gcttattaat tatatgtttt ttaatctttg atcaggggac   2700
aacagtggtt gataacctgt tgaacagtga ggatgtccac tacatgctcg ggccttgag    2760
gactcttggt ctctctgtcg aagcggacaa agctgccaaa agagctgtag ttgttggctg   2820
tggtggaaag ttcccagttg aggattctaa agaggaagtg cagctcttct ggggaatgc    2880
tggaactgca atgcggccat tgacagcagc tgttactgct gctggtggaa atgcaacgta   2940
tgtttcctct ctttctctct acaatacttg ctggagttag tatgaaaccc atgggtatgt   3000
ctagtggctt atggtgtatt ggttttgaa  cttcagttac gtgcttgatg gagtaccaag   3060
aatgagggag agacccattg gcgacttggt tgtcggattg aagcagcttg tgcagatgt    3120
tgattgtttc cttggcactg actgcccacc tgttcgtgtc aatggaatcg gagggctacc   3180
tggtggcaag gttagctact aagggccaca tgttacattc ttctgtaaat ggtacaacta   3240
ttgtcgagct tttgcatttg taaggaaagc attgattgat ctgaatttga tgctacacca   3300
```

Figure 2B

```
caaaatatcc tacaaatggt catccctaac tagcaaacaa tgaagtaata cttggcatgt    3360
gtttatcaaa ttaatttcca tcttctgggg cattgcctgt tttctagtct aatagcattt    3420
gtttttagca ttaattagct cttacaattg ttatgttcta caggtcaagc tgtctggctc    3480
catcagcagt cagtacttga gtgccttgct gatggctgct cctttggctc ttggggatgt    3540
ggagattgaa atcattgata aattaatctc cattccctac gtcgaaatga cattgagatt    3600
gatggagcgt tttggtgtga aagcagagca ttctgatagc tgggacagat tctacattaa    3660
gggaggtcaa aaatacaagt aagctctgta atgtatttca ctactttgat gccaatgttt    3720
cagtttttcag ttttccaaac agtcgcatca atatttgaat agatgcactg tagaaaaaaa    3780
atcattgcag ggaaaaacta gtactgagta ttttgactgt aaattatttt accagtcgga    3840
atatagtcag tctattggag tcaagagcgt gaaccgaaat agccagttaa ttatcccatt    3900
atacagagga caaccatgta tactattgaa acttggttta taagagaatc taggtagctg    3960
gactcgtagc tgcttggcat ggataccttc ttatctttag gaaaagacac ttgatttttt    4020
ttttctgtgg ccctctatga tgtgtgaacc tgcttctcta ttgctttaga aggatatatc    4080
tatgtcgtta tgcaacatgc ttcccttagc catttgtact gaaatcagtt tcataagttc    4140
gttagtggtt ccctaaacga aaccttgttt ttctttgcaa tcaacaggtc ccctaaaaat    4200
gcctatgttg aaggtgatgc ctcaagcgca agctatttct tggctggtgc tgcaattact    4260
ggagggactg tgactgtgga aggttgtggc accaccagtt tgcaggtaaa gatttcttgg    4320
ctggtgctac aataactgct tttgtctttt tggtttcagc attgttctca gagtcactaa    4380
ataacattat catctgcaaa tgtcaaatag acatacttag gtgaattcat gtaaccgttt    4440
ccttacaaat ttgctgaaac ctcaggttga tgtgaagttt gctgaggtac tggagatgat    4500
gggagcgaag gttacatgga ccgagactag cgtaactgtt actgcccac cgcgggagcc    4560
atttgggagg aaacacctca aggcgattga tgtcaacatg aacaagatgc ctgatgtcgc    4620
catgactctt gctgtggttg ccctctttgc cgatggcccg acagccatca gagacggtaa    4680
aacattctca gccctacaac catgcctctt ctacatcact acttgacaag actaaaaact    4740
attggctcgt tggcagtggc ttcctggaga gtaaaggaga ccgagaggat ggttgcgatc    4800
cggacggagc taaccaaggt aaggctacat acttcacatg tctcacgtcg tctttccata    4860
gctcgctgcc tcttagcggc ttgcctgcgg tcgctccatc ctcggttgct gtctgtgttt    4920
tccacagctg ggagcatctg ttgaggaagg gccggactac tgcatcatca cgccgccgga    4980
gaagctgaac gtgacggcga tcgacacgta cgacgaccac aggatggcca tggccttctc    5040
ccttgccgcc tgtgccgagg tccccgtgac catccgggac cctgggtgca cccggaagac    5100
cttccccgac tacttcgatg tgctgagcac tttcgtcaag aattaataaa gcgtgcgata    5160
ctaccacgca gcttgattga agtgataggc ttgtgctgag gaaatacatt tctttttgttc    5220
tgtttttttct ctttcacggg attaagtttt gagtctgtaa cgttagttgt ttgtagcaag    5280
tttctatttc ggatcttaag tttgtgcact gtaagccaaa tttcatttca agagtggttc    5340
gttggaataa taagaataat aaattacgtt tcagtggctg tcaagcctgc tgctacgttt    5400
taggagatgg cattagacat tcatcatcaa caacaataaa acctttagc ctcaaacaat    5460
aatagtgaag ttatttttta gtcctaaaca agttgcatta ggatatagtt aaaacacaaa    5520
agaagctaaa gttagggttt agacatgtgg atattgtttt ccatgtatag tatgttcttt    5580
ctttgagtct catttaacta cctctacaca taccaacttt agtttttttt ctacctcttc    5640
atgttactat ggtgccttct tatcccactg agcattggta tatttagagg ttttttgttga    5700
acatgcctaa atcatctcaa tcaacgatgg acaatctttt cttcgattga gctgaggtac    5760
gtcatctaca ggataggacc ttgagaatat gtgtccgtca atagctaacc ctctactaat    5820
ttttttcaatc aagcaaccta ttggcttgac tttaattcgt accggcttct actacttcta    5880
cagtatttttg tctctataaa ttgcagctac aacagtcaga acggctggct ttaaaatcaa    5940
atggcctaag gatcattgaa aggcatctta gcaatgtcta aaattattac cttctctaga    6000
cgttgatatc                                                          6010
```

Figure 3A

| | | | | | | | | | | | | | |
|---|---|---|---|---|---|---|---|---|---|---|---|---|---|
| Met | Ala | Ala | Met | Ala | Thr | Lys | Ala | Ala | Ala | Gly | Thr | Val | Ser | Leu | Asp |

Met Ala Ala Met Ala Thr Lys Ala Ala Ala Gly Thr Val Ser Leu Asp
1             5                     10                    15
Leu Ala Ala Pro Ser Arg Arg His His Arg Pro Ser Ser Ala Arg Pro
             20                  25                  30
Pro Ala Arg Pro Ala Val Arg Gly Leu Arg Ala Pro Gly Arg Arg Val
             35                  40                  45
Ile Ala Ala Pro Pro Ala Ala Ala Ala Ala Ala Val Gln Ala Gly
    50                  55                  60
Ala Glu Glu Ile Val Leu Gln Pro Ile Lys Glu Ile Ser Gly Thr Val
65                  70                  75                    80
Lys Leu Pro Gly Ser Lys Ser Leu Ser Asn Arg Ile Leu Leu Leu Ala
             85                  90                  95
Ala Leu Ser Glu Gly Thr Thr Val Val Asp Asn Leu Leu Asn Ser Glu
             100                 105                 110
Asp Val His Tyr Met Leu Gly Ala Leu Arg Thr Leu Gly Leu Ser Val
             115                 120                 125
Glu Ala Asp Lys Ala Ala Lys Arg Ala Val Val Val Gly Cys Gly Gly
    130                 135                 140
Lys Phe Pro Val Glu Asp Ser Lys Glu Glu Val Gln Leu Phe Leu Gly
145                 150                 155                   160
Asn Ala Gly Ile Ala Met Arg Ser Leu Thr Ala Ala Val Thr Ala Ala
                 165                 170                 175
Gly Gly Asn Ala Thr Tyr Val Leu Asp Gly Val Pro Arg Met Arg Glu
             180                 185                 190
Arg Pro Ile Gly Asp Leu Val Val Gly Leu Lys Gln Leu Gly Ala Asp
        195                 200                 205
Val Asp Cys Phe Leu Gly Thr Asp Cys Pro Pro Val Arg Val Asn Gly
    210                 215                 220
Ile Gly Gly Leu Pro Gly Gly Lys Val Lys Leu Ser Gly Ser Ile Ser
225                 230                 235                   240
Ser Gln Tyr Leu Ser Ala Leu Leu Met Ala Ala Pro Leu Ala Leu Gly
             245                 250                 255
Asp Val Glu Ile Glu Ile Ile Asp Lys Leu Ile Ser Ile Pro Tyr Val
             260                 265                 270
Glu Met Thr Leu Arg Leu Met Glu Arg Phe Gly Val Lys Ala Glu His
        275                 280                 285
Ser Asp Ser Trp Asp Arg Phe Tyr Ile Lys Gly Gly Gln Lys Tyr Lys
    290                 295                 300
Ser Pro Lys Asn Ala Tyr Val Glu Gly Asp Ala Ser Ser Ala Ser Tyr
305                 310                 315                   320
Phe Leu Ala Gly Ala Ala Ile Thr Gly Gly Thr Val Thr Val Glu Gly
             325                 330                 335
Cys Gly Thr Thr Ser Leu Gln Gly Asp Val Lys Phe Ala Glu Val Leu
        340                 345                 350
Glu Met Met Gly Ala Lys Val Thr Trp Thr Glu Thr Ser Val Thr Val
        355                 360                 365
Thr Gly Pro Pro Arg Glu Pro Phe Gly Arg Lys His Leu Lys Ala Ile
    370                 375                 380
Asp Val Asn Met Asn Lys Met Pro Asp Val Ala Met Thr Leu Ala Val
385                 390                 395                   400
Val Ala Leu Phe Ala Asp Gly Pro Thr Ala Ile Arg Asp Val Ala Ser
             405                 410                 415
Trp Arg Val Lys Glu Thr Glu Arg Met Val Ala Ile Arg Thr Glu Leu
             420                 425                 430

Figure 3B

```
Thr Lys Leu Gly Ala Ser Val Glu Glu Gly Pro Asp Tyr Cys Ile Ile
        435             440             445
Thr Pro Pro Glu Lys Leu Asn Val Thr Ala Ile Asp Thr Tyr Asp Asp
    450             455             460
His Arg Met Ala Met Ala Phe Ser Leu Ala Ala Cys Ala Glu Val Pro
465             470             475             480
Val Thr Ile Arg Asp Pro Gly Cys Thr Arg Lys Thr Phe Pro Asp Tyr
            485             490             495
Phe Asp Val Leu Ser Thr Phe Val Lys Asn
        500             505
```

Western Blots of Soybean and Corn Extracts Using Hybridoma 5E11 Culture Supernatants.
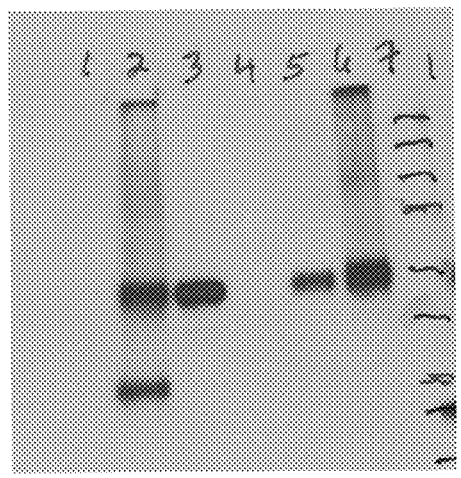
1. Jack (Soy)
2. FG74 (2mEPSPS Soy)
3. 2mEPSPS (.2ug)
4. 963 (Corn)
5. B485 (2mEPSPS Corn)
6. GA21 (2mEPSPS Corn)
7. MW Standards
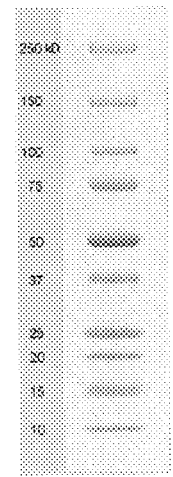
FIGURE 4A
FIGURE 4C
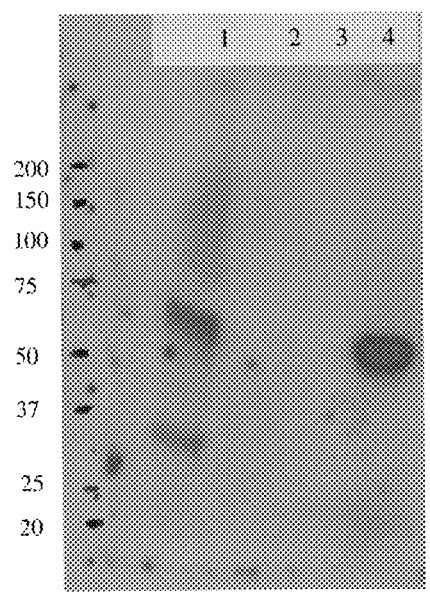
1. FG74 (2mEPSPS Soy)
2. Jack (Soy)
3. RRSoy (CP4)
4. 2mEPSPS (.2ug)
FIGURE 4B ary applications U.S. Ser. No. 61/033,063, filed Mar.

ANTIBODIES IMMUNOREACTIVE WITH MUTANT 5-ENOLPYRUVLSHIKIMATE-3-PHOSPHATE SYNTHASE

REFERENCE TO RELATED APPLICATIONS

This application claims priority to previously filed and co-pending application U.S. Ser. No. 61/033,063, filed Mar. 3, 2008, the contents of which is incorporated by reference in its entirety.

BACKGROUND OF THE INVENTION

Glyphosate (N-phosphonomethylglycine) is a widely used component in herbicides. Glyphosate inhibits 5-enolpyruvyl-3-phosphoshikimic acid synthase (EPSP synthase, or EPSPS), which is involved in the synthesis of aromatic amino acids in plant cells. Inhibition of EPSPS effectively disrupts protein synthesis and thereby kills the affected plant cells. Because glyphosate is non-selective, it kills both weeds and crop plants. Thus it is useful with crop plants when one can modify the crop plants to be resistant to glyphosate, allowing the desirable plants to survive exposure to the glyphosate. Accordingly, there is a need to produce transgenic crop plants that are resistant to glyphosate.

Recombinant DNA technology has been used to isolate mutant EPSP synthases that are glyphosate-resistant. Such glyphosate-resistant mutant EPSP synthases can be transformed into plants and confer glyphosate-resistance upon the transformed plants. By way of example, a glyphosate tolerant gene was isolated from *Agrobacterium* strain CP4 as described in U.S. Pat. No. 5,633,435. This reference and all references cited are incorporated herein by reference.

Other glyphosate tolerant genes have been created through the introduction of mutations. These include those isolated by Comai and described at U.S. Pat. Nos. 5,094,945, 4,769,061 and 4,535,060. A single mutant has been utilized, as described in U.S. Pat. No. 5,310,667 by substituting an alanine residue for a glycine residue at between positions 80 and 120. Double mutants are also described at U.S. Pat. Nos. 6,225,114 and 5,866,775 in which, in addition to the above mutation, a second mutation (a threonine residue for an alanine residue between positions 170 and 210) is introduced into a wild-type EPSPS gene.

Other work resulted in the production of a double mutant EPSPS maize transformation event GA21 through the introduction of a modified maize EPSPS gene bearing mutations at residue 102 (changing threonine to isoleucine) and at residue 106 (changing proline to serine) of the amino acid sequence encoded by GenBank Accession No. X63374 and shown in U.S. Pat. No. 6,566,587 (see sequence identifier number 3 in the '587 patent) and U.S. Pat. No. 6,040,497. In FIG. 1 is shown Genbank accession number X63374 nucleotide sequence, which is the corn EPSPS nucleotide sequence (SEQ ID NO: 1). The amino acid sequence encoded is set forth beneath the nucleotide sequence (SEQ ID NO: 2). Note that an implied ATG start codon is not included at the beginning of X63374 nucleotide sequence. The double mutant sequence is that in which residue 102 of SEQ ID NO: 2 is changed to isoleucine and residue 106 is changed to serine, and the resulting double mutant protein is SEQ ID NO: 3.

In U.S. Pat. No. 7,045,684, a genomic EPSPS fragment was isolated from maize and subsequently two mutations were introduced into the corn EPSPS gene which resulted in the same mutated EPSPS protein as above, in event GA21. Using the corn EPSPS gene, Genbank accession number X63374, as a probe, a 6.0 kb genomic fragment was isolated, that fragment shown here in FIGS. 2A and 2B and is SEQ ID NO: 4. Two mutations were introduced into this nucleotide sequence; the first a cytosine to thymine substitution at nucleotide 2886, and the second a cytosine to thymine substitution at nucleotide 2897 (the positions are in bold and underlined in FIGS. 2A and 2B and the mutated nucleotide sequence is SEQ ID NO: 5). This resulted in an encoded mutant amino acid which is shown in FIGS. 3A and 3B and is SEQ ID NO: 6 with the residue at position 164 (position 102 of the amino acid of X63374/SEQ ID NO: 3) changed from threonine to isoleucine (Thr to Ile) and at position 168 (position 106 of the amino acid of X63374/SEQ ID NO: 3) changed from proline to serine (Pro to Ser). The resulting mutated amino acid sequence was glyphosate resistant.

The mutated nucleotide sequence of SEQ ID NO: 5 includes the native corn EPSPS promoter, coding region (containing the two mutations), introns and 3' terminator region. The GA21 event, supra, on the other hand, used a rice actin promoter (McElroy et al. (1990) *Plant Cell* 2:163-171) and nos terminator (Depicker et al., (1982) *Mol. and Appl. Genet.* 1:561-573). However, both coding sequences essentially produce the same mutated protein having the change of threonine to isoleucine at position 102 of the protein and proline to serine at position 106 of the protein.

There is a need to identify antibodies that are immunoreactive with the double mutant EPSPS proteins described above so that plants containing such mutated EPSPS proteins can be readily identified. Especially useful would be an antibody that immunoreacts with the double mutant EPSPS protein containing the mutations at residue 102 (Thr to Ile) and at position 106 (Pro to Ser) and is not reactive with the CP4 enzyme, a version used in various commercial glyphosate resistant products, nor with the wild-type EPSPS protein. A method that would avoid time-consuming lab steps would reduce costs, allowing for quick identification of the transgenic plants containing the mutant protein, aiding in breeding and selection. Furthermore, antibodies that are immunoreactive with such proteins could be useful in isolating and purifying the proteins.

SUMMARY OF THE INVENTION

The invention is directed to hybridomas and the antibodies and fragments produced from the hybridomas, which are immunoreactive with the amino acid sequence of a double mutant EPSPS gene. The amino acid sequence is that which substitutes an isoleucine for threonine at position 102 and substitutes a serine for proline at position 106 of the protein of GenBank accession number X63374, which is shown in SEQ ID NO: 3, and also with the corresponding mutations in SEQ ID NO 6. Use of the antibodies to identify plant cells having said amino acids and to isolate and purify same are also disclosed.

BRIEF DESCRIPTION OF THE DRAWINGS

FIG. 1 is the sequence as set forth in Genbank accession number X63374, which is the corn EPSPS nucleotide sequence and is SEQ ID NO: 1; below the nucleotide sequence is indicated the encoded amino acid sequence encoded which is SEQ ID NO: 2. Residues 102 and 106 are in bold and underlined; substitution of isoleucine for threonine at 102 and substitution of serine for proline at position 106 of the protein is the double mutant EPSPS and is SEQ ID NO: 3.

FIGS. 2A and 2B shows the genomic fragment of corn EPSPS isolated and is SEQ ID NO: 4. Mutations introduced at positions 2886 in which thymine is substituted for cytosine and at position 2897 in which thymine is substituted for cytosine are in bold and underlined; the mutated nucleotide sequence is SEQ ID NO: 5.

FIGS. 3A and 3B shows the amino acid sequence which is encoded by the mutant nucleotide sequence of SEQ ID NO: 5 and is SEQ ID NO: 6.

FIG. 4A is a Western blot showing the immunological reaction of MAb5E11 with "Jack" a soybean not having the double mutant EPSPS; with FG74, a soybean having the double mutant EPSPS; with the isolated double mutant EPSPS protein; with 963, corn not having the double mutant EPSPS; with B485, corn having the double mutant EPSPS; with another corn having the double mutant EPSPS, GA21. This figure also includes the molecular weight standards in lane 7. FIG. 4B is a Western Blot showing immunoreactivity of MAb5E11 with the soybean FG74 having the double mutant EPSPS, with Jack, the soybean not having the double mutant; with a Roundup-Ready® soybean containing the glyphosate resistant EPSPS enzyme from Agrobacterium tumefaciens strain CP4; and isolated double mutant EPSPS. FIG. 4C shows the relevant molecular weight standards.

DETAILED DESCRIPTION OF EMBODIMENTS OF THE INVENTION

Described here are hybridomas and monoclonal antibodies and fragments of same, prepared from these hybridomas against a double mutant 5-endopyruvylshikimate-3-phosphate synthase (EPSPS) enzyme. The monoclonal antibodies immunoreactive with and are useful to identify presence of the enzyme, and to isolate and purify the enzyme. The monoclonal antibodies are particularly useful in that they distinguish between a wild-type EPSPS enzyme (that is, the EPSPS which would be naturally occurring in non-transformed plants) and a double mutant EPSPS enzyme. Terms used herein employ their common definitions; for example, immunoreactive refers to reacting to particular antigens or haptens, and wild-type refers to the polypeptide as it occurs in nature.

A double mutant EPSPS enzyme is one in which, compared to the wild-type endogenous EPSPS, there are two mutations in the amino acid of the enzyme. The double mutant here is also referred to as 2mEPSPS. As shown in the examples below, the monoclonal antibody is immunoreactive to a EPSPS protein containing isoleucine at residue 102 and serine at residue 106. This sequence is shown in FIG. 1 with the mutation positions bolded and underlined and is SEQ ID NO: 3. As can be seen in FIG. 1, the corn EPSPS gene is set forth and is SEQ ID NO: 1. The amino acid sequence it encodes is set forth beneath the nucleotide sequence and is SEQ ID NO: 2. The amino acid sequence is with the two mutations as indicated is SEQ ID NO: 3. The residue mutations of SEQ ID NO: 6 versus SEQ ID NO: 3 occur because in SEQ ID NO: 3, the amino acid or residues are shown without the N-terminal chloroplast transit peptide. The form of the EPSP synthase with the transit peptide when expressed is delivered to the chloroplast, where the transit peptide is cleaved yielding the version of EPSP synthase without the peptide. Reference to the numbering of residues of the EPSP amino acid (without chloroplast transit peptide leader) is used in examples here not to limit the invention, but to facilitate comparison of EPSPS sequences from sources which have chloroplast transit peptides (i.e., plants and fungi) to sources which do not utilize a chloroplast targeting signal (i.e., bacteria). As used herein when referring to the "antibody" or "monoclonal antibody" (MAb) of the invention is meant an antibody or fragment of same that is immunoreactive with a double mutant EPSPS amino acid sequence having said mutation.

An antibody (or an immunoglobulin) is a protein synthesized by an animal in response to the presence of a foreign substance that is called an antigen. Each antibody molecule has a unique structure that enables it to bind specifically to its corresponding antigen, but all antibodies have the same overall structure. An antibody molecule is composed of two distinct regions. One is a constant region and the other is a variable region that gives an antibody the specificity to a vast variety of different antigens.

Five major classes of antibodies are IgM, IgD, IgG, IgA, and IgE. IgG is the most abundant class. IgG, as an example, has a molecular weight of 150 kDa and is composed of two different types of polypeptide chains: one is the heavy chain (50 kDa) and the other is the light chain (25 kDa). Each IgG molecule has two heavy chains and two light chains linked by disulfide bonds. Variable regions of the heavy ($V_H$) and light ($V_L$) chains together function as the variable region of the antibody and give the antibody the ability to bind a specific antigen.

In the amino acid sequences discussed here, the standard single letter or three letter nomenclature are used. All peptide structures represented in the following description are shown in conventional format in which the amino group at the N-terminus appears to the left and the carboxyl group at the C-terminus at the right. Likewise, amino acid nomenclature for the naturally occurring amino acids found in protein is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser; S), threonine (Thr,T), tryptophan (Trp;W), tyrosine (Tyr;Y), and valine (Val;V). An "X" may be used when the amino acid residue is unknown and parentheses designate that an unambiguous assignment is not possible and the amino acid designation within the parentheses is the most probable estimate based on known information.

Deoxyribonucleic acid (DNA) is a polymer comprising four mononucleotide units, DAMP (2'-Deoxyadenosine-5-monophosphate), dGMP (2'-Deoxyguanosine-5-monophosphate), dCMP (2'-Deoxycytosine-5-monophosphate) and dTMP (2'-Deoxycytosine-5-monophosphate) linked in various sequences by 3',5'-phosphodiester bridges. The structural DNA consists of multiple nucleotide triplets called "codons" which code for the amino acids. The codons correspond to the various amino acids as follows: Arg (CGA, CGC, CGG, CGT, AGA, AGG); Leu (CTA, CTC, CTG, CTT, TTA, TTG); Ser (TCA, TCC, TCG, TCT, AGC, AGT); Thr (ACA, ACC, ACG, ACT); Pro (CCA, CCC, CCG, CCT); Ala (GCA, GCC, GCG, GCT); Gly (GGA, GGC, GGG, GGT); Ile (ATA, ATC, ATT); Val (GTA, GTC, GTG, GTT); Lys (AAA, AAG); Asn (AAC, AAT); Gln (GAA, CAG); His (CAC, CAT); Glu (GAA, GAG); Asp (GAC, GAT); Tyr (TAC, TAT); Cys (TGC, TGT); Phe (TTC, TTT); Met (ATG); and Trp (UGG). Moreover, due to the redundancy of the genetic code (i.e., more than one codon for all but two amino acids), there are many possible DNA sequences which may code for a particular amino acid sequence.

The use of somatic hybrid cell lines as sources of antibody to individual antigens generally dates from the work of Kohler and Milstein (Nature 256:495-97 (1975)). The antibodies produced are quite different than those recovered from antiserum from conventionally immunized animals. Each hybrid cell line synthesizes a homogenous immunoglobulin that represents but one of the myriad of types of antibodies that an animal can synthesize in response to an antigen in vivo. Since each immunoglobulin-producing clone is characterized by the single type of antibody it produces, the term monoclonal antibody has been adopted. The advantages of monoclonal antibodies are numerous; they can be obtained in large supply; the preparation is homogenous with respect to antigen reactivity and remains so over time.

The principle of hybridoma/monoclonal technology is predicated on the observation that when two somatic cells are fused the resultant hybrid displays characteristics of both of the parent cell types. In the case of monoclonal antibody production, the ability to synthesize the particular antibody is derived from an immunocompetent cell (usually a spleen cell) taken from an immunized donor animal, whereas the ability to continuously divide in cell culture is contributed by the other fusion partner, a tumor cell line (often a myeloma). Early fusions were complicated by the fact that myeloma cell line also produced a monoclonal antibody; thus the hybrid often produced two types of monoclonal antibody, one of myeloma origin and the other directed by the genetic information of the immunocompetent cell. Subsequently, tumor cells lines incapable of producing their own monoclonal have been used, e.g., SP2/0-Ag14 or X63-Ag8.653, thereby simplifying the analysis of the resultant fusion products.

Another technical consideration involves the rationale for selecting the successful fusion events (hybrid cells) from the two types of parental cells. Routinely a million or more cells of each type are used in the fusion protocol, and since fusion does not occur with 100% frequency, the job of trying to recover fusion products from the high background of unfused or self-fused parents can be formidable. As mentioned hybridomas are formed by the fusion of short-lived antibody producing (spleen) cells and long-lived myeloma cells. The desired result is a long-lived cell line which produces antibody. Since the spleen cells have a finite life span in culture one can simply wait an appropriate period for all the nonfused or self-fused spleen cells to die; however one must still recover from the resultant population the long-lived antibody producing cells from the long-lived antibody non-producing cells. A popular means for selection hybrid cells is the so-called HAT-selection system. This system involves the use of the enzyme hypoxanthine-guanine-phosphoribosyl transferase (HGPRT). This enzyme functions in the purine salvage pathway in mammalian cells. These cells are also capable of synthesizing purines de novo. Under most conditions, both pathways probably operate to a certain extent. If a cell lacks HGPRT, the salvage pathway is blocked and purines must be manufactured from non-purine materials.

The chemical 8-azaguanine is an antimetabolite which is capable of masquerading as the purine guanine and replacing it in some of its normal reactions. Azaguanine is incorporated into DNA, interfering with the normal growth pattern and leading to cell death. Since azaguanine must be salvaged, any cell which lacks HGPRT activity cannot utilize azaguanine and will grow in its presence.

A selective system which operates on the same enzyme but in the opposite sense in that HGPRT positive cells are selected is described by J. W. Littlefield (*Science*, 145: 709 (1964)). It is called HAT and contains hypoxanthine, aminopterin and thymidine (HAT medium). Aminopterin is an antimetabolite that prevents de novo purine synthesis and methylation of deoxyuridylate to form thymidylate. Hypoxanthine can serve as a salvagable purine in the event that aminopterin blocks de novo purine biosynthesis while thymidine bypasses the necessity for the methylation of thymidylate. Thus, in the presence of aminopterin, any cell with positive HGPRT activity will proliferate while cells with negative HGPRT activity will die.

I In a hybrid system which can be used for selection in accordance with the invention, the myeloma cells are resistant to azaguanine and susceptible to aminopterin, that is, they are HGPRT negative. Thus, they will die in the presence of aminopterin. The antibody producing cells are HGPRT positive. By fusing the cells and growing them in HAT medium without azaguanine (HT medium), the successfully fused cells are selected because the myeloma cells which constitute the proliferating line can only grow where HGPRT activity is present and this activity must be supplied by the HGPRT positive cell line. The antibody producing HGPRT positive cell line are not killed in this medium. They will live for a time but will not proliferate.

Thus, by fusing the cells in a HAT medium, systems are produced in which the myeloma cells and antibody producing cells can grow long enough to produce hybrid cells but in which only the hybrid cells can survive and proliferate. After selection each hybridoma clone is then screened for the ability to produce the particular antibody of interest.

A double mutant EPSPS protein was purified and used as the antigen in the preparation of the 2mEPSP synthase-specific monoclonal antibody. In one embodiment, a preparation process is characterized in that: a) an extract is made from parts of the plants containing a double mutant EPSPS enzyme, preserved at low temperature by grinding, centrifugation and filtration, b) the extract obtained is enriched in EPSPS protein by precipitation in an appropriate solvent, centrifugation and solubilisation of the precipitate obtained in a buffer solution, c) the active protein thus obtained is purified by chromatography and if desired, d) the hybridomas and monoclonal antibodies are prepared from an antigen solution obtained from one of the preparations obtained in paragraphs a), b), and c) above, e) the hybridomas are screened and the monoclonal antibody or antibodies directed specifically against the double mutant EPSPS are selected.

In describing the above is not meant to limit the production of the antibodies of the invention to such precise systems; as further methods of such antibody production are developed and optimized they are well within the scope of the invention.

The monoclonal antibodies so isolated can be used in a variety of ways. As demonstrated below, the antibodies can distinguish between plant tissue containing the double mutant, and those which do not contain the double mutant, including wild-type plant protein and protein having the CP4 enzyme. Thus the antibodies can be used to identify those plant cells, tissue and plants which contain the double mutant, thus allowing for selection of such plants without destroying the plant nor requiring extensive field tests.

Kits useful with the invention may take any of a variety of forms and in general provide for obtaining an amino acid containing sample from plant tissue, a support having affixed to it the antibody of the invention capable of forming a binary complex with the 2mEPSPS which may be present in the sample, and a binary complex detecting means. The specifics of the kit beyond employing the antibody or fragment immunoreactive properties of the invention are not critical. The method or means of obtaining the amino acid containing sample is not critical, and can take any form, as long as a plant sample is obtained; the detecting means likewise can take any of a myriad of forms, as is well appreciated by one skilled in the art. Detecting means have been used for some time, and can include, for example, biotin, a fluorescent dye, a radio isotope or an enzyme.

In one embodiment, for example, the monoclonal antibody may be applied to a support structure, such as a test strip. By way of example without intending to limit the application of the invention, the antibody may be use with an immunostrip. One antibody is conjugated to a gold particle and applied to a fiber pad. A second antibody is striped as a line onto a membrane. A strip is assembled in such a way as that a sample pad is placed into the sample extract and the antigen is wicked up the strip, coming in contact with the conjugated MAb and later with the striped MAb. The striped MAb "captures" the antigen-conjugate complex forming a colored line. If no antigen is present, no line forms. A kit would comprise materials required to perform a test for 2mEPSPS.

When using such a process to identify the presence of the 2mEPSPS protein in a corn plant (from which the 2mEPSPS was originally derived), the exposure of the antibody to the protein and detecting agent should be such that the results of the tests are not misinterpreted due to potential cross-reactivity with the background amino acid of the corn plant. For example, an ELISA or enzyme linked immunoassay may be used, an assay known since 1971. While specifics can differ, in general, antigens solubilized in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate. Thus, in one embodiment, when assaying corn plant samples, the ELISA test should continue to the point that presence of the mutant protein can be determined, if present, yet not so long that high background presence of the corn wild-type gene in any particular sample causes an increase in positive results not entirely attributable to the presence of 2mEPSPS. While the antibodies of the invention can be minimally immunoreactive to wild-type corn EPSPS, these antibodies are more highly immunoreactive to the mutant EPSPS, and this may need no change to the process, or for most optimal results, adjustments may be desired when corn, as opposed to soybean or other plant tissue is sampled. In one example the ELISA test is allowed to run up to about 30 minutes, and to about 90 minutes in a further embodiment. The timing need not be precise, and specifics can be determined in advance for any particular situation.

In the event precise determinations for presence of the mutant are required, other tests are well known to one skilled in the art. By way of example, without limitation, a Western Blot analysis is among the type of test that may be employed. A Western analysis is a variation of the Southern analysis technique. With a Southern analysis, DNA is cut with restriction endonucleases and fractionated on an agarose gel to separate the DNA by molecular weight and then transferring to nylon membranes. It is then hybridized with the probe fragment which was radioactively labeled with $^{32}P$ and washed in an SDS solution. In the Western analysis, instead of isolating DNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" *Molecular Breeding* 3:291-306 (1997).

Another way the MAbs can be used is in a double antibody sandwich ELISA. The antigen-antibody interactions are similar to those of the immunostrip but take place in the wells of a polystyrene plate.

The antibodies may also be used in purifying and isolating the double mutant EPSPS amino acids. For example, samples containing double mutant EPSPS enzymes may be passed through a chromatography column containing the monoclonal antibodies of the invention such that the enzymes bind to and are isolated from other amino acids in the sample.

Clearly the antibodies of the invention may be employed in a variety of uses, a few of which are exemplified here, and which are known to those skilled in the art.

The following are presented by way of illustration and are not intended to limit the scope of the invention.

EXPERIMENTAL

Isolation of His-Tagged 2mEPSPS Protein

Isolation of the 2mEPSPS protein expressed in bacteria used standard protocols as provided by Qiagen, Inc. (The QIAexpressionist™: A handbook for high-level expression and purification of 6xHis-tagged proteins. Fifth Edition, 2003)

The protocol used in summarized as follows. First, the lysate was loaded on the column in a buffer B.

Buffer B consists of (1 liter):
   100 mM $NaH_2PO_4$
   13.8 g $NaH_2PO_4*H_2O$ (MW 137.99 g/mol)
   10 mM Tris*Cl 1.2 g Tris base (MW 121.1 g/mol) and
   8 M urea 480.5 g (MW 60.06 g/mol).

pH was adjusted to 8.0 using NaOH. There followed a wash with buffer B up to zero absorption at 280 nm. A further wash with buffer C was carried out.

Buffer C consists of (1 liter):
   100 mM $NaH_2PO4$
   13.8 g $NaH_2PO4*H_2O$ (MW 137.99 g/mo)
   10 mM Tris*Cl
   1.2 g Tris base (MW 121.1 g/mol) and
   8 M urea 480.5 g (MW 60.06 g/mol).

pH was adjusted to 6.3 using HCl. The column was eluted with minimal volume with buffer E.

Buffer E (1 liter) consists of:
   100 mM $NaH_2PO4$
   13.8 g $NaH_2PO4*H_2O$ (MW 137.99 g/mol)
   10 mM Tris*Cl
   1.2 g Tris base (MW 121.1 g/mol) and
   8 M urea 480.5 g (MW 60.06 g/mol).

Adjustment of pH to 4.5 was carried out using HCl. Adjusting the pH of solutions just before use is very important.

The expression level of the protein is estimated as 20 mg/L in a combination of soluble and insoluble fractions. It is also possible to resolublize the insoluble fraction.

The purified EPSPS protein (provided at 1.5 mg/mL) was precipitated. The protein concentration in the supernatant was quantitated by Micro BCA Protein Assay Reagent Kit (PIERCE, #23235) and was 0.121 mg/mL. The precipitate was saved for refolding.

Refolding Procedures

The refolding procedures were performed using Protein Refolding Kit from Novagen (Fisher, #NC98068050) following the suggested protocol. At room temperature, 1 mL of 10× IB Solubilization Buffer was added to 8.89 mL of deionized water, then added with 0.1 mL of 30% N-lauroylsarcosine and 10 μL of 1M DTT. 1 mL of prepared 1× Solubilization Buffer/N-lauroylsarcosine was added to the precipitate and gently mixed. The mixture was incubated for 15 minutes at room temperature and centrifuged at 10,000×g for 10 minutes. Then the supernatant was dialyzed in 1× Dialysis Buffer with 0.1 mM DTT at 4° C. for three hours. The buffer was changed and the dialysis was continued for another three hours at the same condition. Then the dialysis was continued with the same dialysis buffer without DTT at 4° C. for three hours with two additional changes.

The refolded protein was quantitated using BCA Protein Assay Reagent Kit (PIERCE, #23235) and the concentration was approximately 0.494 mg/mL. This protein was used for the immunization. The sera of the immunized mice were tested against both the original protein in the supernatant (0.121 mg/mL) and the refolded protein (0.494 mg/mL), and no recognizable difference between their reactivities was seen.

Production of Antibodies

Balb/c mice were primed and boosted three to four times with purified corn EPSPS every two to four weeks. Complete and incomplete Freund's Adjuvant were used for the priming and the boosting respectively. After two boosts, serum titers were monitored by ELISA. Once the titers were high enough, splenocytes were harvested from the immunized mice and fused with myeloma cells (P3/NSI/1-Ag4-1) using PEG1500 as a fusion agent. The resulting cell fusion products were diluted in hybridoma medium and seeded into 96-well tissue culture plates. After one day, HAT medium was added to the hybridoma cultures. The medium was changed every three or four days as necessary. After ten to fourteen days of culture with selection, screening was initiated by ELISA. Two fusions were completed.

Antibodies were screened against soybean leaf extract (1:20 in PBS/TWEEN® 20 (polysorbate (20) sorbitan monolaurate, a surfactant)) that was genetically modified to express corn 2mEPSPS protein, wild-type soybean leaf extract (1:20 in PBS/TWEEN® 20), and 6×His-KLH. Ninety-six well Nunc Maxi-sorp Immunoplates™ (Nunc # 446612, Roskilde, Denmark) were coated by adding 50 μl per well of solution of the extracts from modified and wild-type soybean leaf and by adding 50 μl per well of 0.5 μg/ml solution of 6×His-KLH in coating buffer (BupH™. Carbonate-Bicarbonate Buffer, Pierce # 28382, Rockford, Ill.) for one hour at room temperature. The coating buffer was removed and the plate was blocked by adding 250 μl per well of blocking buffer (1% Blocker, TM. BSA, Pierce # 37525, in PBS) for two hours at room temperature. 50 μl of hybridoma supernatant were added into the wells and incubated for one hour at room temperature. Wells were washed four times with PBS/TWEEN® 20. 50 μl of diluted (1:7,000) HRP-conjugated goat anti-mouse Ig (Southern Biotech #1010-05) was added into the wells and incubated for one hour at room temperature. The wells were washed five times with PBS/TWEEN® 20. Anti-EPSPS antibodies were detected by adding 50 μl per well of TMB (tetramethyl benzidine) solution (ImmunoPure®. TMB Substrate Kit, Pierce #34021) for 5 to 10 minutes. Plates were read spectorphotometrically at 450 nm using a microplate reader (Molecular Devices, Sunnyvale, Calif.).

Following the screenings of two fusion products by ELISA, antibodies showing specific binding to 2mEPSPS were selected.

Western Blot Analysis of Selected Antibodies

The activities of selected antibodies were further confirmed by Western Blot Assay. Purified 2mEPSPS and the extract from nontransgenic soybean leaf were separated by sodium dodecyl sulfate-polyacrylamide gel electrophoresis (SDS-PAGE) under reducing, blotted onto nitrocellulose membrane and probed with twenty antibodies. In detail, 12% bis-tris gel was used (NuPAGE Novex 1 well #NP0344BOX) in Xcell SureLock Mini-Cell system (Invitrogen #EI0001) and after electrophoresis, protein is transferred to nitrocellulose membrane. The blotted membrane was then incubated with the twenty antibodies using Mini-PROTEIN II Multi-screen Apparatus system (Bio-Rad #170-4017) and further developed using goat anti-mouse Ig-alkaline phosphatase conjugate and BCIP/NPT as a substrate. Antibodies were also tested by Western Blot Assay using purified 2mEPSPS, non-transgenic corn (963) and 2mEPSPS corn (B485 and GA21). Antibodies demonstrating specificity for the 2mEPSPS protein were selected for further screening by ELISA (see below).

ELISA Screening

Monoclonal antibodies derived from hybridomas produced against 2mEPSPS were screened using an indirect DAS ELISA format. Briefly, plates were coated with a polyclonal antibody specific for EPSPS. Extracts of non-GMO Corn, 2mEPSPS corn(B485), GA21, and Roundup Ready® (CP4) Soybean were then incubated in the plate overnight. The plates were then incubated with 2mEPSPS specific monoclonal antibodies and then detected with alkaline phosphatase labeled rabbit anti mouse IgG. Monoclonal antibodies showing specificity for 2mEPSPS (not native corn EPSPS) were chosen for further study. Nine antibodies designated 21F2, 12H1, 12E1, 10B9, 10B5, 9E12, 7A9, 7A8, and 5E11 were selected finally for their assay development. Subcloning was performed for the clones that express the nine antibodies. Results of one such screening is shown below.

The designation "4 μg/ml G0268R" refers to the polyclonal EPSPS antibody which was coated on the plate at 4 μg/ml. The category "EPSPS μg/ml" refers to a standard curve made up from 2mEPSPS that was expressed in *E. coli* and purified.

Colorimetric response was recorded as optical density (OD) by an ELISA plate reader at a wavelength of 405 nM. This particular assay was read after 90 minutes of substrate development. Longer development produces a concomitant increase in background (non GMO corn) as well as higher OD readings for the 2mEPSPS. MAbs 10B5.B4, 10B9.E8, 12H1.B1, and especially 5E11.11 demonstrated specificity for 2mEPSPS.

| EPSPS MAb Screen 4 ug/ml G0268R 90 min | | | | |
|---|---|---|---|---|
| EPSPS ug/ml | 5E11.E11 | 10B5.B4 | 10B9.E8 | 12H1.B1 |
| 1 | 1.261 | 1.529 | 1.544 | 1.387 |
| 0.5 | 0.786 | 1.082 | 1.097 | 1.024 |
| 0.25 | 0.446 | 0.635 | 0.688 | 0.599 |
| 0.125 | 0.237 | 0.355 | 0.373 | 0.346 |
| 0.0625 | 0.154 | 0.226 | 0.242 | 0.208 |
| Buffer | 0.057 | 0.068 | 0.066 | 0.063 |
| Non GMO Corn | 0.092 | 0.127 | 0.152 | 0.136 |
| B485 GMO Corn | 0.461 | 0.587 | 0.823 | 0.734 |
| GA21 GMO Corn | 0.932 | 1.130 | 1.140 | 1.021 |
| RR-CP4 Soy | 0.056 | 0.074 | 0.086 | 0.070 |

Western Blot Analysis Comparisons

Specificity of the reactivity of the antibodies was confirmed by Western Blot Assay. Extracts were obtained from soybean plant not transformed with the mutant EPSPS (labeled "Jack"); and corn not transformed with the mutant EPSPS (labeled "963"); as well as lines transformed with the 2mEPSPS encoding sequences. Such lines transformed with the mutant included GA21 (see supra, U.S. Pat. Nos. 6,566, 587 and 6,040,497), B485 (see U.S. Pat. No. 7,045,684) and the glyphosate resistant soybean line FG74 which is generated by introducing a corn 2mepsps gene (similar to the one used in GA21) by particle gun bombardment. (Described generally at Klein, T. M., Arentzen, R., Lewis, P. A. and Fitzpatrick-McElligott, S. (1992) Transformation of microbes, plants and animals by particle bombardment. *Biotechnology* (N Y) 10, 286-291.).

Extracts were also obtained from a soybean plant expressing the EPSPS protein providing glyphosate resistance, CP4, supra, U.S. Pat. No. 5,633,435. Purified corn EPSPS and the extract from the identified plants were separated by sodium dodecyl sulfate-polyacrylamide gel electrophoresis (SDS-PAGE) under reducing, blotted onto nitrocellulose membrane and probed with the monoclonal antibody 5E11 In general, 8-16% Pierce Precise gel was used in Bio-Rad Mini Protean 3 apparatus at 15mA/gel until the samples are completely in gel, and then at 30 mA/gel. The gels were transferred to PVDF membrane. Detection of proteins is performed using the Zymed Western Blot Kit (#96-9045).

A protein with an apparent molecular weight of 50 kD was identified by SDS-PAGE (See FIGS. 4A-4C) and matches molecular weight of the 2mEPSPS protein sequence. As can be seen in FIG. 4A, the MAb 5E11 is specific for the 2mEPSPS in soybean, and corn and also with the extracted 2mEPSPS. It is does not react with corn and soybean not transformed with the 2mEPSPS. Further, FIG. 4B shows that MAb5E11 is immunoreactive with a 2mEPSPS soybean and the purified mutant protein, but does not react with the CP4 protein.

Embodiments of the Invention

In an embodiment the invention is directed to a hybridoma cell line selected from the group consisting of 10B5.B4, 10B9.E8, 12H1.B1 and 5E11.E11 which is deposited as ATCC Nos. PTA-8900; PTA-8901; PTA-8902; and PTA-8903. An embodiment is to an antibody or fragment thereof produced by the any one of said hybridomas.

Still further embodiments are to an antibody or fragment thereof immunoreactive with a double mutant EPSPS amino acid sequence, said sequence produced by changing a threonine to isoleucine at residue 102 and changing a proline to serine at residue 106 of the EPSPS protein. In an embodiment the amino acid with which the antibody or fragment thereof is immunoreactive is that produced by providing for such substitution at the residues of SEQ ID NO: 2. An embodiment provides the antibody or fragment is one immunoreactive with the mutant amino acid of SEQ ID NO: 3. An embodiment provides the antibody or fragment is one immunoreactive with the amino acid shown at by Genbank accession number X63374. In a still further embodiment the antibody or fragment thereof is one immunoreactive with an amino acid encoded by the double mutant nucleotide sequence of SEQ ID NO: 5. An embodiment provides for an antibody or fragment thereof immunoreactive with the mutant amino acid sequence of SEQ ID NO: 6. Further embodiments provide that said antibody or fragment is not immunoreactive with wild-type EPSPS amino acid. Additional embodiments provide said antibody or fragment is not immunoreactive with the CP4 enzyme.

Additional embodiments provide for a method of generating an antibody or fragment thereof, the method comprising immunizing an animal with an amino acid selected from the group consisting of the amino acids defined above, recovering splenocytes from the immunized animal, fusing the splenocytes with myleoma cells, recovering monoclonal hybridomas, and producing a monoclonal antibody or fragment thereof immunoreactive with said amino acid.

Another embodiment of the invention provides for a method for detecting the presence of a double mutant EPSPS amino acid selected from the amino acids as defined in above, the method comprising contacting a composition comprising said amino acid with an antibody or fragment thereof selected from the group of antibodies as defined above, and determining whether the amino acid is bound by said antibody or fragment thereof.

Further embodiments provide for a kit for detecting the presence of a mutated EPSPS amino acid selected from the group consisting of the amino acids as defined above, in a sample comprising an antibody or fragment thereof selected from the group of antibodies as defined above, and a detection agent. Additional embodiments provide the detection agent may be selected from the group consisting of biotin, a fluorescent dye, a radio isotope and an enzyme.

Yet further embodiments provide that that the kit further comprises:
(i) a means for obtaining an amino acid containing sample from plant tissue;
(ii) a support having affixed thereto said monoclonal antibody which is capable of forming a binary complex with said mutated EPSPS amino acid which may be present in the sample; and
(iii) a binary complex detecting means.

An embodiment provides for a monoclonal antibody produced by exposing an animal to a mutated EPSPS amino acid selected from the group of mutant EPSPS amino acids defined above, and obtaining an antibody.

What is claimed is:

1. An antibody immunoreactive with a mutated EPSPS (5-enolpyruvyl-3-phosphoshikimic acid synthase) polypeptide, wherein said antibody is selected from the group consisting of:
   (a) an antibody immunoreactive with a mutated EPSPS polypeptide wherein said mutated EPSPS polypeptide when compared to a wild-type EPSPS polypeptide comprises a first mutation wherein an isoleucine amino acid is substituted for the amino acid which corresponds to residue 102 of said wild-type EPSPS polypeptide and a second mutation wherein a serine amino acid is substituted for the amino acid which corresponds to residue 106 of said wild-type EPSPS polypeptide;
   (b) an antibody immunoreactive with a mutated EPSPS polypeptide wherein said mutated EPSPS polypeptide when compared with SEQ ID NO: 2 comprises a first mutation wherein an isoleucine amino acid is substituted for the amino acid which corresponds to residue 102 of said SEQ ID NO: 2, and a second mutation wherein a serine amino acid is substituted for the amino acid which corresponds to residue 106 of said SEQ ID NO: 2;
   (c) an antibody immunoreactive with a polypeptide comprising the polypeptide encoded by SEQ ID NO: 5;
   (d) an antibody immunoreactive with a polypeptide comprising SEQ ID NO: 3;
   (e) an antibody immunoreactive with a polypeptide comprising SEQ ID NO: 6;
   (f) an antibody produced by a hybridoma selected from the group consisting of 10B5.B4 assigned ATCC Number PTA-8900, 10B9.E8 assigned ATCC number PTA-8901, 12H1.B1 assigned ATCC number 8902, and 5E11.E11 assigned ATCC number PTA-8903; and
   (g) a fragment of an antibody of (a), (b), (c), (d), (e) or (f) wherein said fragment is immunoreactive with a mutated EPSPS polypeptide selected from the group consisting of the polypeptides of (a), (b), (c), (d), and (e).

2. The antibody of claim 1, wherein said antibody is immunoreactive with the polypeptide of SEQ ID NO: 3.

3. The antibody of claim 1, wherein said antibody is immunoreactive with the polypeptide of SEQ ID NO: 6.

4. The antibody of claim 1, wherein said antibody is immunoreactive with the polypeptide encoded by SEQ ID NO: 5.

5. The antibody of claim 1, wherein said antibody is immunoreactive with a mutated EPSPS polypeptide wherein said mutated EPSPS polypeptide when compared with a wild-type EPSPS comprises a first mutation wherein an isoleucine amino acid is substituted for the amino acid which corresponds to residue 102 of said wild-type EPSPS polypeptide and a second mutation wherein a serine amino acid is substituted for the amino acid which corresponds to residue 106 of said wild-type EPSPS polypeptide.

6. The antibody of claim 1, wherein said wild-type EPSPS polypeptide is SEQ ID NO: 2.

7. The antibody of claim 1, wherein said antibody is not immunoreactive with endogenous soybean wild-type EPSPS polypeptide.

8. The antibody of claim 1, wherein said antibody is not immunoreactive with *Agrobacterium* strain CP4 enzyme.

9. The antibody of claim 1, wherein said antibody binds with a higher affinity to said mutated polypeptide than to endogenous corn wild-type EPSPS polypeptide.

10. The antibody of claim 1, wherein said antibody binds with a higher affinity to said mutated polypeptide than to a endogenous corn wild-type polypeptide, is not immunoreactive with endogenous soybean wild-type polypeptide and is not immunoreactive with *Agrobacterium* strain CP4 enzyme.

11. A hybridoma cell line selected from the group consisting of 10B5.B4 assigned ATCC Number PTA-8900, 10B9.E8 assigned ATCC number PTA-8901, 12H1.B1 assigned ATCC number 8902, and 5E11.E11 assigned ATCC number PTA-8903.

12. A method for detecting the presence of a mutated EPSPS (5-enolpyruvyl-3-phosphoshikimic acid synthase) polypeptide in a composition, the method comprising contacting said composition with the antibody of claim 1, and determining whether the antibody is immunoreactive with any of said mutated EPSPS polypeptide in said composition.

13. The method of claim 12, wherein said antibody is not immunoreactive with endogenous soybean wild-type EPSPS polypeptide.

14. The method of claim 12, wherein said antibody binds with a higher affinity to said mutated polypeptide than to endogenous corn wild-type EPSPS polypeptide.

15. The method of claim 12, wherein said antibody is not immunoreactive with *Agrobacterium* strain CP4 enzyme.

16. The antibody of claim 12, wherein said antibody is more highly immunoreactive with said mutated polypeptide than to endogenous corn wild-type polypeptide, is not immunoreactive with endogenous soybean wild-type polypeptide and is not immunoreactive with *Agrobacterium* strain CP4 enzyme.

17. A method of generating an antibody, the method comprising
   (a) immunizing an animal with a polypeptide selected from the group consisting of
      (i) a mutated EPSPS (5-enolpyruvyl-3-phosphoshikimic acid synthase) polypeptide wherein said mutated EPSPS polypeptide when compared to a wild-type EPSPS polypeptide comprises a first mutation wherein an isoleucine amino acid is substituted for the amino acid which corresponds to residue 102 of said wild-type EPSPS polypeptide and a second mutation wherein a serine amino acid is substituted for the amino acid which corresponds to residue 106 of said wild-type EPSPS polypeptide,
      (ii) a mutated EPSPS polypeptide wherein said mutated EPSPS polypeptide when compared with SEQ ID NO: 2 comprises a first mutation wherein an isoleucine amino acid is substituted for the amino acid which corresponds to residue 102 of said SEQ ID NO: 2, and a second mutation wherein a serine amino acid is substituted for the amino acid which corresponds to residue 106 of said SEQ ID NO: 2,
      (iii) a polypeptide comprising the polypeptide encoded by SEQ ID NO: 5,
      (iv) an EPSPS polypeptide comprising the polypeptide of SEQ ID NO: 3,
      (v) an EPSPS polypeptide comprising the polypeptide of SEQ ID NO: 6, and
      (vi) a fragment of a polypeptide of (i), (ii), (iii), (iv) or (v) wherein said fragment generates an antibody in said animal immunoreactive to a polypeptide selected from the polypeptide of (i), (ii), (iii), (iv) and (v);
   (b) recovering splenocytes from the immunized animal;
   (c) fusing said splenocytes with myleoma cells to produce monoclonal hybridomas; and
   (d) producing monoclonal antibodies from said hybridoma.

18. A kit for detecting the presence of a mutated EPSPS (5-enolpyruvyl-3-phosphoshikimic acid synthase) polypeptide in a composition, the kit comprising the antibody of claim 1, and a detection agent.

19. The kit of claim 18, wherein said kit further comprises
   (i) a plant sample obtaining device;
   (ii) a support having affixed thereto said antibody which is capable of forming a binary complex with said mutated EPSPS polypeptide which may be present in said sample; and
   (iii) a binary complex detecting means.

* * * * *

SEQUENCE LISTING

```
<160> NUMBER OF SEQ ID NOS: 6

<210> SEQ ID NO 1
<211> LENGTH: 1335
<212> TYPE: DNA
<213> ORGANISM: Zea mays
<220> FEATURE:
<221> NAME/KEY: CDS
<222> LOCATION: (1)..(1332)

<400> SEQUENCE: 1 gcg ggt gcc gag gag atc gtg ctg cag ccc atc aag gag atc tcc ggc      48
Ala Gly Ala Glu Glu Ile Val Leu Gln Pro Ile Lys Glu Ile Ser Gly
```

```
        1               5                   10                  15
acc gtc aag ctg ccg ggg tcc aag tcg ctt tcc aac cgg atc ctc cta    96
Thr Val Lys Leu Pro Gly Ser Lys Ser Leu Ser Asn Arg Ile Leu Leu
             20                  25                  30 ctc gcc gcc ctg tcc gag ggg aca aca gtg gtt gat aac ctg ctg aac   144
Leu Ala Ala Leu Ser Glu Gly Thr Thr Val Val Asp Asn Leu Leu Asn
         35                  40                  45 agt gag gat gtc cac tac atg ctc ggg gcc ttg agg act ctt ggt ctc   192
Ser Glu Asp Val His Tyr Met Leu Gly Ala Leu Arg Thr Leu Gly Leu
     50                  55                  60 tct gtc gaa gcg gac aaa gct gcc aaa aga gct gta gtt gtt ggc tgt   240
Ser Val Glu Ala Asp Lys Ala Ala Lys Arg Ala Val Val Val Gly Cys
65                  70                  75                  80 ggt gga aag ttc cca gtt gag gat gct aaa gag gaa gtg cag ctc ttc   288
Gly Gly Lys Phe Pro Val Glu Asp Ala Lys Glu Glu Val Gln Leu Phe
                 85                  90                  95 ttg ggg aat gct gga act gca atg cgg cca ttg aca gca gct gtt act   336
Leu Gly Asn Ala Gly Thr Ala Met Arg Pro Leu Thr Ala Ala Val Thr
            100                 105                 110 gct gct ggt gga aat gca act tac gtg ctt gat gga gta cca aga atg   384
Ala Ala Gly Gly Asn Ala Thr Tyr Val Leu Asp Gly Val Pro Arg Met
        115                 120                 125 agg gag aga ccc att ggc gac ttg gtt gtc gga ttg aag cag ctt ggt   432
Arg Glu Arg Pro Ile Gly Asp Leu Val Val Gly Leu Lys Gln Leu Gly
    130                 135                 140 gca gat gtt gat tgt ttc ctt ggc act gac tgc cca cct gtt cgt gtc   480
Ala Asp Val Asp Cys Phe Leu Gly Thr Asp Cys Pro Pro Val Arg Val
145                 150                 155                 160 aat gga atc gga ggg cta cct ggt ggc aag gtc aag ctg tct ggc tcc   528
Asn Gly Ile Gly Gly Leu Pro Gly Gly Lys Val Lys Leu Ser Gly Ser
                165                 170                 175 atc agc agt cag tac ttg agt gcc ttg ctg atg gct gct cct ttg gct   576
Ile Ser Ser Gln Tyr Leu Ser Ala Leu Leu Met Ala Ala Pro Leu Ala
            180                 185                 190 ctt ggg gat gtg gag att gaa atc att gat aaa tta atc tcc att ccg   624
Leu Gly Asp Val Glu Ile Glu Ile Ile Asp Lys Leu Ile Ser Ile Pro
        195                 200                 205 tac gtc gaa atg aca ttg aga ttg atg gag cgt ttt ggt gtg aaa gca   672
Tyr Val Glu Met Thr Leu Arg Leu Met Glu Arg Phe Gly Val Lys Ala
    210                 215                 220 gag cat tct gat agc tgg gac aga ttc tac att aag gga ggt caa aaa   720
Glu His Ser Asp Ser Trp Asp Arg Phe Tyr Ile Lys Gly Gly Gln Lys
225                 230                 235                 240 tac aag tcc cct aaa aat gcc tat gtt gaa ggt gat gcc tca agc gca   768
Tyr Lys Ser Pro Lys Asn Ala Tyr Val Glu Gly Asp Ala Ser Ser Ala
                245                 250                 255 agc tat ttc ttg gct ggt gct gca att act gga ggg act gtg act gtg   816
Ser Tyr Phe Leu Ala Gly Ala Ala Ile Thr Gly Gly Thr Val Thr Val
            260                 265                 270 gaa ggt tgt ggc acc acc agt ttg cag ggt gat gtg aag ttt gct gag   864
Glu Gly Cys Gly Thr Thr Ser Leu Gln Gly Asp Val Lys Phe Ala Glu
        275                 280                 285 gta ctg gag atg atg gga gcg aag gtt aca tgg acc gag act agc gta   912
Val Leu Glu Met Met Gly Ala Lys Val Thr Trp Thr Glu Thr Ser Val
    290                 295                 300 act gtt act ggc cca ccg cgg gag cca ttt ggg agg aaa cac ctc aag   960
Thr Val Thr Gly Pro Pro Arg Glu Pro Phe Gly Arg Lys His Leu Lys
305                 310                 315                 320 gcg att gat gtc aac atg aac aag atg cct gat gtc gcc atg act ctt  1008
```

-continued

```
Ala Ile Asp Val Asn Met Asn Lys Met Pro Asp Val Ala Met Thr Leu
            325                 330                 335 gct gtg gtt gcc ctc ttt gcc gat ggc ccg aca gcc atc aga gac gtg    1056
Ala Val Val Ala Leu Phe Ala Asp Gly Pro Thr Ala Ile Arg Asp Val
                340                 345                 350 gct tcc tgg aga gta aag gag acc gag agg atg gtt gcg atc cgg acg    1104
Ala Ser Trp Arg Val Lys Glu Thr Glu Arg Met Val Ala Ile Arg Thr
        355                 360                 365 gag cta acc aag ctg gga gca tct gtt gag gaa ggg ccg gac tac tgc    1152
Glu Leu Thr Lys Leu Gly Ala Ser Val Glu Glu Gly Pro Asp Tyr Cys
    370                 375                 380 atc atc acg ccg ccg gag aag ctg aac gtg acg gcg atc gac acg tac    1200
Ile Ile Thr Pro Pro Glu Lys Leu Asn Val Thr Ala Ile Asp Thr Tyr
385                 390                 395                 400 gac gac cac agg atg gcc atg gcc ttc tcc ctt gcc gcc tgt gcc gag    1248
Asp Asp His Arg Met Ala Met Ala Phe Ser Leu Ala Ala Cys Ala Glu
                405                 410                 415 gtc ccc gtc acc atc cgg gac cct ggg tgc acc cgg aag acc ttc ccc    1296
Val Pro Val Thr Ile Arg Asp Pro Gly Cys Thr Arg Lys Thr Phe Pro
            420                 425                 430 gac tac ttc gat gtg ctg agc act ttc gtc aag aat taa                1335
Asp Tyr Phe Asp Val Leu Ser Thr Phe Val Lys Asn
        435                 440

<210> SEQ ID NO 2
<211> LENGTH: 444
<212> TYPE: PRT
<213> ORGANISM: Zea mays

<400> SEQUENCE: 2

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
```

-continued

```
             210                 215                 220
Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ile Thr Gly Gly Thr Val Thr Val
            260                 265                 270

Glu Gly Cys Gly Thr Thr Ser Leu Gln Gly Asp Val Lys Phe Ala Glu
            275                 280                 285

Val Leu Glu Met Met Gly Ala Lys Val Thr Trp Thr Glu Thr Ser Val
290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
                340                 345                 350

Ala Ser Trp Arg Val Lys Glu Thr Glu Arg Met Val Ala Ile Arg Thr
            355                 360                 365

Glu Leu Thr Lys Leu Gly Ala Ser Val Glu Glu Gly Pro Asp Tyr Cys
370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
                420                 425                 430

Asp Tyr Phe Asp Val Leu Ser Thr Phe Val Lys Asn
            435                 440

<210> SEQ ID NO 3
<211> LENGTH: 444
<212> TYPE: PRT
<213> ORGANISM: Zea mays

<400> SEQUENCE: 3

Ala Gly Ala Glu Glu Ile Val Leu Gln Pro Ile Lys Glu Ile Ser Gly
  1               5                  10                  15

Thr Val Lys Leu Pro Gly Ser Lys Ser Leu Ser Asn Arg Ile Leu Leu
                20                  25                  30

Leu Ala Ala Leu Ser Glu Gly Thr Thr Val Val Asp Asn Leu Leu Asn
            35                  40                  45

Ser Glu Asp Val His Tyr Met Leu Gly Ala Leu Arg Thr Leu Gly Leu
50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Ile Ala Met Arg Ser Leu Thr Ala Ala Val Thr
            100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Lys Gln Leu Gly
        130                 135                 140
```

-continued

```
Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
            165                 170                 175

Ile Ser Ser Gln Tyr Leu Ser Ala Leu Leu Met Ala Ala Pro Leu Ala
        180                 185                 190

Leu Gly Asp Val Glu Ile Glu Ile Asp Lys Leu Ile Ser Ile Pro
        195                 200                 205

Tyr Val Glu Met Thr Leu Arg Leu Met Glu Arg Phe Gly Val Lys Ala
210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440
```

<210> SEQ ID NO 4
<211> LENGTH: 6010
<212> TYPE: DNA
<213> ORGANISM: Zea mays

<400> SEQUENCE: 4

| | | |
|---|---|---|
| atcgattgca accttcaaat tctcttcgat cttccttcca aattcatcta atatttcatc | 60 |
| ctcggcaagg aaatcttcta acgtgtaaac ttcactggga tccaactcga aaggatcaaa | 120 |
| ctctccctct ggttcgtttg acattgtgga tggagtgact aacctgctaa cacccctgcaa | 180 |
| caatttatac aggagcatat cctcatgcac acgcaaaact gatgttgtcc acaagacacg | 240 |
| cacaggacac gcacaggaca cgcaaacagt ttcagactca tgcacacgca catcagtttc | 300 |
| agactcaggc acacgcacat caaatcacct tcgcttgtcg atgagtcgca gccgcatcgt | 360 |
| acaatggcga ttttaccgac gataaggcat gggagcacga gccgtcgccg tcgccttgcg | 420 |

```
agacgacggg agcgatctct cccttcattt aatctcttcc acgtcaggtt attttgctga    480
gatggcagta tacagacggc aaagttaatg ccgttgtaca tgcccttaga ctcttccgtc    540
accaactcac ttagattttt acaacggaac ataaggttcg cttgcagact tacatataag    600
gtatagttgc ataataatcg ccttatgctg tacattgcga cacccgtaaa tattcgatga    660
aatattagta cacaatatta ataagaacg aacaatacat atattatcat tgatcttagt    720 atctccttt gctcctcgta gaacaattct gtgtaaatta tgcgtaaaat tcgaggacca    780
aaacattggc tagaaaaata cctaaaatca gttttgcaat tgtttctgat tttcctcata    840
ttttcttgct tataaagttt tccaaaagta ccattttgga tgaaaaaacg gaaacaacg     900 ctggtctact tgtaaatttg gtagtgacat ttgggaccgt ctagacacga cctaaaaata    960
gtagtctaaa acatagtctg acacgatgcc ttaaaaatag acgacaaagc acaacacgat   1020
tagatgtgtc gtgttttgac cgacacgaca caaagtaagg cacgatttaa acccaataa    1080 ataatatttt aatggttatt ttatgttcca ataattttca tctcttcaaa aaatgttat    1140 agaaatcatt gatacttagt tgaatatcct aacacaatat atatatatat attaatatat   1200
atatatatca attttaagtc actttgctag acatagtaat atattttaaa tattttctct   1260
ttcttgtata ttttaaaat acacatcagt ttttatatgt gtcgtgcttg aaccgacacg    1320
atataatcat cggttcgccg tacttctaga tcatgatgtt cctaggtttt aatattaaga   1380
gacggtctat attaactcaa aactatttcg tgaaaggcta actcgaaaaa aaaatgaatg   1440
taatcacggc ccgtcctgga ttcgagattc taacgtttca ttcgtgtcca gtgtgcacac   1500
ttgtggaaaa ggaagacgaa gaaaaaaacc aacaactaac tccggcccgc cggatgcgcc   1560
cacctacttc cccctcgccc ctctcatggt ctctctcgcg cccagatctg ctactagacg   1620
gcaccgctgc agcgcgtcgt gtcgcggggg ttggtggcag gcagcgagag cttgccgttc   1680
ctctctctca gttgtcaggt cctaggctca cctcaccggc tcccagcccg cttctatttc   1740
ttcctccccg accccgtgca ggtggcagtc cagtccacgc caccaaccgc gaggcgaacc   1800
aaaccaaccc actctcccca accccgcgcg cccaggccgc ccgccctacc aaccatcggc   1860
gtcggcaatg gcggccatgg cgaccaaggc cgccgcgggc accgtgtcgc tggacctcgc   1920
cgcgccgtcg cgccgccacc accgcccgag ctcggcgcgc ccgcccgccc gccccgccgt   1980
ccgcgggctg cgggcgcctg ggcgccgcgt gatcgccgcg ccgccggcgg cggcagcggc   2040
ggcggcggtg caggcgggtg ccgaggagat cgtgctgcag cccatcaagg agatctccgg   2100
caccgtcaag ctgccggggt ccaagtcgct ttccaaccgg atcctcctgc tcgccgccct   2160
gtccgaggtg agcgatttg tgtgcttgct cgctgccctg tctcactgct acctaaatgt   2220
tttgcctgtc gaataccatg gattctcggt gtaatccatc tcacgatcag atgcaccgca   2280
tgtcgcatgc ctagctctct ctaatttgtc tagtagtttg tatacggatt aatattgata   2340
aatcggtacc gcaaaagcta ggtgtaaata acactagaa aattggatgt tcccctatcg    2400
gcctgtactc ggctactcgt tcttgtgatg gcatgctgtc tcttcttggt gtttggtgaa   2460
caaccttatg aaatttgggc gcaaagaact cgccctcaag ggttgatctt atgccatcgt   2520
catgataaac agtggagcac ggacgatcct ttacgttgtt tttaacaaac tttgtcagaa   2580
aactagcatc attaacttct taatgacgat ttcacaacaa aaaaggtaa cctcgctact    2640 aacataacaa aatacttgtt gcttattaat tatatgtttt ttaatctttg atcaggggac   2700
aacagtggtt gataacctgt tgaacagtga ggatgtccac tacatgctcg ggcctttgag   2760
gactcttggt ctctctgtcg aagcggacaa agctgccaaa agagctgtag ttgttggctg   2820
```

```
tggtggaaag ttcccagttg aggattctaa agaggaagtg cagctcttct tggggaatgc    2880
tggaactgca atgcggccat tgacagcagc tgttactgct gctggtggaa atgcaacgta    2940
tgtttcctct ctttctctct acaatacttg ctggagttag tatgaaaccc atgggtatgt    3000
ctagtggctt atggtgtatt ggttttgaa cttcagttac gtgcttgatg gagtaccaag    3060
aatgagggag agacccattg gcgacttggt tgtcggattg aagcagcttg gtgcagatgt    3120
tgattgtttc cttggcactg actgcccacc tgttcgtgtc aatggaatcg gagggctacc    3180
tggtggcaag gttagctact aagggccaca tgttacattc ttctgtaaat ggtacaacta    3240
ttgtcgagct tttgcatttg taaggaaagc attgattgat ctgaatttga tgctacacca    3300
caaaatatcc tacaaatggt catccctaac tagcaaacaa tgaagtaata cttggcatgt    3360
gtttatcaaa ttaatttcca tcttctgggg cattgcctgt tttctagtct aatagcattt    3420 gttttagca ttaattagct cttacaattg ttatgttcta caggtcaagc tgtctggctc    3480
catcagcagt cagtacttga gtgccttgct gatggctgct cctttggctc ttggggatgt    3540
ggagattgaa atcattgata aattaatctc cattccctac gtcgaaatga cattgagatt    3600
gatggagcgt tttggtgtga agcagagca ttctgatagc tgggacagat tctacattaa    3660
gggaggtcaa aaatacaagt aagctctgta atgtatttca ctactttgat gccaatgttt    3720
cagttttcag ttttccaaac agtcgcatca atatttgaat agatgcactg tagaaaaaaa    3780
atcattgcag ggaaaaacta gtactgagta ttttgactgt aaattatttt accagtcgga    3840
atatagtcag tctattggag tcaagagcgt gaaccgaaat agccagttaa ttatcccatt    3900
atacagagga caaccatgta tactattgaa acttggttta aagagaatc taggtagctg    3960 gactcgtagc tgcttggcat ggataccttc ttatctttag gaaaagacac ttgatttttt    4020
ttttctgtgg ccctctatga tgtgtgaacc tgcttctcta ttgctttaga aggatatatc    4080
tatgtcgtta tgcaacatgc ttcccttagc catttgtact gaaatcagtt tcataagttc    4140
gttagtggtt ccctaaacga aaccttgttt ttctttgcaa tcaacaggtc ccctaaaaat    4200
gcctatgttg aaggtgatgc ctcaagcgca agctatttct tggctggtgc tgcaattact    4260
ggagggactg tgactgtgga aggttgtggc accaccagtt tgcaggtaaa gatttcttgg    4320
ctggtgctac aataactgct tttgtctttt tggtttcagc attgttctca gagtcactaa    4380
ataacattat catctgcaaa tgtcaaatag acatacttag gtgaattcat gtaaccgttt    4440
ccttacaaat ttgctgaaac ctcagggtga tgtgaagttt gctgaggtac tggagatgat    4500
gggagcgaag gttacatgga ccgagactag cgtaactgtt actggcccac cgcgggagcc    4560
atttgggagg aaacacctca aggcgattga tgtcaacatg aacaagatgc ctgatgtcgc    4620
catgactctt gctgtggttg ccctctttgc cgatggcccg acagccatca gagacggtaa    4680
aacattctca gccctacaac catgcctctt ctacatcact acttgacaag actaaaaact    4740
attggctcgt tggcagtggc ttcctggaga gtaaaggaga ccgagaggat ggttgcgatc    4800
cggacggagc taaccaaggt aaggctacat acttcacatg tctcacgtcg tctttccata    4860
gctcgctgcc tcttagcggc ttgcctgcgg tcgctccatc ctcggttgct gtctgtgttt    4920
tccacagctg ggagcatctg ttgaggaagg gccggactac tgcatcatca cgccgccgga    4980
gaagctgaac gtgacggcga tcgacacgta cgacgaccac aggatggcca tggccttctc    5040
ccttgccgcc tgtgccgagg tccccgtgac catcccggac cctgggtgca cccggaagac    5100
cttccccgac tacttcgatg tgctgagcac tttcgtcaag aattaataaa gcgtgcgata    5160
```

-continued

```
ctaccacgca gcttgattga agtgataggc ttgtgctgag gaaatacatt tcttttgttc    5220
tgttttttct ctttcacggg attaagtttt gagtctgtaa cgttagttgt ttgtagcaag    5280
tttctatttc ggatcttaag tttgtgcact gtaagccaaa tttcatttca agagtggttc    5340
gttggaataa taagaataat aaattacgtt tcagtggctg tcaagcctgc tgctacgttt    5400
taggagatgg cattagacat tcatcatcaa caacaataaa accttttagc ctcaaacaat    5460
aatagtgaag ttatttttta gtcctaaaca agttgcatta ggatatagtt aaaacacaaa    5520
agaagctaaa gttagggttt agacatgtgg atattgtttt ccatgtatag tatgttcttt    5580
ctttgagtct catttaacta cctctacaca taccaacttt agtttttttt ctacctcttc    5640
atgttactat ggtgccttct tatcccactg agcattggta tatttagagg ttttttgttga   5700 acatgcctaa atcatctcaa tcaacgatgg acaatctttt cttcgattga gctgaggtac    5760
gtcatctaca ggataggacc ttgagaatat gtgtccgtca atagctaacc ctctactaat    5820
tttttcaatc aagcaaccta ttggcttgac tttaattcgt accggcttct actacttcta    5880
cagtattttg tctctataaa ttgcagctac aacagtcaga acggctggct ttaaaatcaa    5940
atggcctaag gatcattgaa aggcatctta gcaatgtcta aaattattac cttctctaga    6000
cgttgatatc                                                            6010

<210> SEQ ID NO 5
<211> LENGTH: 6010
<212> TYPE: DNA
<213> ORGANISM: Zea mays

<400> SEQUENCE: 5
atcgattgca accttcaaat tctcttcgat cttccttcca aattcatcta atatttcatc      60
ctcggcaagg aaatcttcta acgtgtaaac ttcactggga tccaactcga aaggatcaaa     120
ctctccctct ggttcgtttg acattgtgga tggagtgact aacctgctaa caccctgcaa     180
caatttatac aggagcatat cctcatgcac acgcaaaact gatgttgtcc acaagacacg     240
cacaggacac gcacaggaca cgcaaacagt ttcagactca tgcacacgca catcagtttc     300
agactcaggc acacgcacat caaatcacct tcgcttgtcg atgagtcgca gccgcatcgt     360
acaatggcga ttttaccgac gataaggcat gggagcacga gccgtcgccg tcgccttgcg     420
agacgacggg agcgatctct cccttcattt aatctcttcc acgtcaggtt attttgctga     480
gatggcagta tacagacggc aaagttaatg ccgttgtaca tgcccttaga ctcttccgtc     540
accaactcac ttagattttt acaacggaac ataaggttcg cttgcagact tacatataag     600
gtatagttgc ataataatcg ccttatgctg tacattgcga cacccgtaaa tattcgatga     660
aatattagta cacaatatta aataagaacg aacaatacat atattatcat tgatcttagt     720
atctcctttt gctcctcgta gaacaattct gtgtaaatta tgcgtaaaat tcgaggacca     780
aaacattggc tagaaaaata cctaaaatca gttttgcaat tgtttctgat ttcctcata     840 ttttcttgct tataaagttt tccaaagta ccattttgga tgaaaaacg gaaaacaacg     900 ctggtctact tgtaaatttg gtagtgacat ttgggaccgt ctagacacga cctaaaaata    960
gtagtctaaa acatagtctg acacgatgcc ttaaaaatag acgacaaagc acaacacgat    1020
tagatgtgtc gtgttttgac cgacacgaca caaagtaagg cacgatttaa acccaataa    1080 ataatatttt aatggttatt ttatgttcca ataattttca tctcttcaaa aaaatgttat    1140
agaaatcatt gatacttagt tgaatatcct aacacaatat atatatat attaatatat    1200 atatatatca attttaagtc actttgctag acatagtaat atattttaaa tatttctct    1260
```

-continued

```
ttcttgtata tttttaaaat acacatcagt ttttatatgt gtcgtgcttg aaccgacacg    1320
atataatcat cggttcgccg tacttctaga tcatgatgtt cctaggtttt aatattaaga    1380
gacggtctat attaactcaa aactatttcg tgaaaggcta actcgaaaaa aaaatgaatg    1440
taatcacggc ccgtcctgga ttcgagattc taacgtttca ttcgtgtcca gtgtgcacac    1500
ttgtggaaaa ggaagacgaa gaaaaaaacc aacaactaac tccggcccgc cggatgcgcc    1560
cacctacttc cccctcgccc ctctcatggt ctctctcgcg cccagatctg ctactagacg    1620
gcaccgctgc agcgcgtcgt gtcgcggggg ttggtggcag gcagcgagag cttgccgttc    1680
ctctctctca gttgtcaggt cctaggctca cctcaccggc tcccagcccg cttctatttc    1740
ttcctccccg accccgtgca ggtggcagtc cagtccacgc caccaaccgc gaggcgaacc    1800
aaaccaaccc actctcccca accccgcgcg cccaggccgc ccgccctacc aaccatcggc    1860
gtcggcaatg gcggccatgg cgaccaaggc cgccgcgggc accgtgtcgc tggacctcgc    1920
cgcgccgtcg cgccgccacc accgcccgag ctcggcgcgc ccgcccgccc gccccgccgt    1980
ccgcgggctg cgggcgcctg ggcgccgcgt gatcgccgcg ccgccggcgg cggcagcggc    2040
ggcggcggtg caggcgggtg ccgaggagat cgtgctgcag cccatcaagg agatctccgg    2100
caccgtcaag ctgccggggt ccaagtcgct ttccaaccgg atcctcctgc tcgccgccct    2160
gtccgaggtg agcgattttg gtgcttgctg cgctgccctg tctcactgct acctaaatgt    2220
tttgcctgtc gaataccatg gattctcggt gtaatccatc tcacgatcag atgcaccgca    2280
tgtcgcatgc ctagctctct ctaatttgtc tagtagtttg tatacggatt aatattgata    2340
aatcggtacc gcaaaagcta ggtgtaaata aacactagaa aattggatgt tcccctatcg    2400
gcctgtactc ggctactcgt tcttgtgatg gcatgctgtc tcttcttggt gtttggtgaa    2460
caaccttatg aaatttgggc gcaaagaact cgccctcaag ggttgatctt atgccatcgt    2520
catgataaac agtggagcac ggacgatcct ttacgttgtt tttaacaaac tttgtcagaa    2580
aactagcatc attaacttct taatgacgat ttcacaacaa aaaaaggtaa cctcgctact    2640
aacataacaa aatacttgtt gcttattaat tatatgtttt ttaatctttg atcagggac    2700 aacagtggtt gataacctgt tgaacagtga ggatgtccac tacatgctcg ggccttgag    2760 gactcttggt ctctctgtcg aagcggacaa agctgccaaa agagctgtag ttgttggctg    2820
tggtggaaag ttcccagttg aggattctaa agaggaagtg cagctcttct tggggaatgc    2880
tggaattgca atgcggtcat tgacagcagc tgttactgct gctggtggaa atgcaacgta    2940
tgtttcctct ctttctctct acaatacttg ctggagttag tatgaaaccc atgggtatgt    3000
ctagtggctt atggtgtatt ggtttttgaa cttcagttac gtgcttgatg gagtaccaag    3060
aatgagggag agacccattg gcgacttggt tgtcggattg aagcagcttg gtgcagatgt    3120
tgattgtttc cttggcactg actgccacc tgttcgtgtc aatggaatcg gagggctacc    3180
tggtggcaag gttagctact aagggccaca tgttacattc ttctgtaaat ggtacaacta    3240
ttgtcgagct tttgcatttg taaggaaagc attgattgat ctgaatttga tgctacacca    3300
caaaatatcc tacaaatggt catccctaac tagcaaacaa tgaagtaata cttggcatgt    3360
gtttatcaaa ttaatttcca tcttctgggg cattgcctgt tttctagtct aatagcattt    3420 gttttagca ttaattagct cttacaattg ttatgttcta caggtcaagc tgtctggctc    3480
catcagcagt cagtacttga gtgccttgct gatggctgct cctttggctc ttggggatgt    3540
ggagattgaa atcattgata aattaatctc cattccctac gtcgaaatga cattgagatt    3600
```

```
gatggagcgt tttggtgtga aagcagagca ttctgatagc tgggacagat tctacattaa  3660
gggaggtcaa aaatacaagt aagctctgta atgtatttca ctactttgat gccaatgttt  3720
cagttttcag ttttccaaac agtcgcatca atatttgaat agatgcactg tagaaaaaaa  3780
atcattgcag ggaaaaacta gtactgagta ttttgactgt aaattatttt accagtcgga  3840
atatagtcag tctattggag tcaagagcgt gaaccgaaat agccagttaa ttatcccatt  3900
atacagagga caaccatgta tactattgaa acttggtttta aagagaatc taggtagctg  3960
gactcgtagc tgcttggcat ggataccttc ttatctttag gaaaagacac ttgatttttt  4020
ttttctgtgg ccctctatga tgtgtgaacc tgcttctcta ttgctttaga aggatatatc  4080
tatgtcgtta tgcaacatgc ttcccttagc catttgtact gaaatcagtt cataagttc   4140
gttagtggtt ccctaaacga aaccttgttt ttctttgcaa tcaacaggtc ccctaaaaat  4200
gcctatgttg aaggtgatgc ctcaagcgca agctatttct tggctggtgc tgcaattact  4260
ggagggactg tgactgtgga aggttgtggc accaccagtt tgcaggtaaa gatttcttgg  4320
ctggtgctac aataactgct tttgtctttt tggtttcagc attgttctca gagtcactaa  4380
ataacattat catctgcaaa tgtcaaatag acatacttag gtgaattcat gtaaccgttt  4440
ccttacaaat ttgctgaaac ctcagggtga tgtgaagttt gctgaggtac tggagatgat  4500
gggagcgaag gttacatgga ccgagactag cgtaactgtt actggcccac cgcgggagcc  4560
atttgggagg aaacacctca aggcgattga tgtcaacatg aacaagatgc ctgatgtcgc  4620
catgactctt gctgtggttg ccctctttgc cgatggcccg acagccatca gagacggtaa  4680
aacattctca gccctacaac catgcctctt ctacatcact acttgacaag actaaaaact  4740
attggctcgt tggcagtggc ttcctggaga gtaaaggaga ccgagaggat ggttgcgatc  4800
cggacggagc taaccaaggt aaggctacat acttcacatg tctcacgtcg tctttccata  4860
gctcgctgcc tcttagcggc ttgcctgcgg tcgctccatc ctcggttgct gtctgtgttt  4920
tccacagctg ggagcatctg ttaggaagg gccggactac tgcatcatca cgccgccgga   4980
gaagctgaac gtgacggcga tcgacacgta cgacgaccac aggatggcca tggccttctc  5040
ccttgccgcc tgtgccgagg tccccgtgac catccgggac cctgggtgca cccggaagac  5100
cttccccgac tacttcgatg tgctgagcac tttcgtcaag aattaataaa gcgtgcgata  5160
ctaccacgca gcttgattga agtgataggc ttgtgctgag gaaatacatt tcttttgttc  5220
tgttttttct ctttcacggg attaagtttt gagtctgtaa cgttagttgt ttgtagcaag  5280
tttctatttc ggatcttaag tttgtgcact gtaagccaaa tttcatttca agagtggttc  5340
gttggaataa taagaataat aaattacgtt tcagtggctg tcaagcctgc tgctacgttt  5400
taggagatgg cattagacat tcatcatcaa caacaataaa accttttagc ctcaaacaat  5460
aatagtgaag ttattttta gtcctaaaca agttgcatta ggatatagtt aaaacacaaa   5520
agaagctaaa gttagggttt agacatgtgg atattgtttt ccatgtatag tatgttcttt  5580
ctttgagtct catttaacta cctctacaca taccaacttt agtttttttt ctacctcttc  5640
atgttactat ggtgccttct tatcccactg agcattggta tatttagagg ttttgttga   5700
acatgcctaa atcatctcaa tcaacgatgg acaatctttt cttcgattga gctgaggtac  5760
gtcatctaca ggataggacc ttgagaatat gtgtccgtca atagctaacc ctctactaat  5820
tttttcaatc aagcaaccta ttggcttgac tttaattcgt accggcttct actacttcta  5880
cagtattttg tctctataaa ttgcagctac aacagtcaga acggctggct ttaaaatcaa  5940
atggcctaag gatcattgaa aggcatctta gcaatgtcta aaattattac cttctctaga  6000
```
cgttgatatc                                                                                  6010

<210> SEQ ID NO 6
<211> LENGTH: 506
<212> TYPE: PRT
<213> ORGANISM: Zea mays

<400> SEQUENCE: 6

Met Ala Ala Met Ala Thr Lys Ala Ala Gly Thr Val Ser Leu Asp
  1               5                  10                  15

Leu Ala Ala Pro Ser Arg Arg His His Arg Pro Ser Ser Ala Arg Pro
                 20                  25                  30

Pro Ala Arg Pro Ala Val Arg Gly Leu Arg Ala Pro Gly Arg Arg Val
             35                  40                  45

Ile Ala Ala Pro Pro Ala Ala Ala Ala Ala Val Gln Ala Gly
 50                  55                  60

Ala Glu Glu Ile Val Leu Gln Pro Ile Lys Glu Ile Ser Gly Thr Val
 65                  70                  75                  80

Lys Leu Pro Gly Ser Lys Ser Leu Ser Asn Arg Ile Leu Leu Leu Ala
                 85                  90                  95

Ala Leu Ser Glu Gly Thr Thr Val Val Asp Asn Leu Leu Asn Ser Glu
                100                 105                 110

Asp Val His Tyr Met Leu Gly Ala Leu Arg Thr Leu Gly Leu Ser Val
            115                 120                 125

Glu Ala Asp Lys Ala Ala Lys Arg Ala Val Val Gly Cys Gly Gly
            130                 135                 140

Lys Phe Pro Val Glu Asp Ser Lys Glu Val Gln Leu Phe Leu Gly
145                 150                 155                 160

Asn Ala Gly Ile Ala Met Arg Ser Leu Thr Ala Ala Val Thr Ala Ala
                165                 170                 175

Gly Gly Asn Ala Thr Tyr Val Leu Asp Gly Val Pro Arg Met Arg Glu
            180                 185                 190

Arg Pro Ile Gly Asp Leu Val Val Gly Leu Lys Gln Leu Gly Ala Asp
            195                 200                 205

Val Asp Cys Phe Leu Gly Thr Asp Cys Pro Pro Val Arg Val Asn Gly
210                 215                 220

Ile Gly Gly Leu Pro Gly Gly Lys Val Lys Leu Ser Gly Ser Ile Ser
225                 230                 235                 240

Ser Gln Tyr Leu Ser Ala Leu Leu Met Ala Ala Pro Leu Ala Leu Gly
                245                 250                 255

Asp Val Glu Ile Glu Ile Ile Asp Lys Leu Ile Ser Ile Pro Tyr Val
            260                 265                 270

Glu Met Thr Leu Arg Leu Met Glu Arg Phe Gly Val Lys Ala Glu His
            275                 280                 285

Ser Asp Ser Trp Asp Arg Phe Tyr Ile Lys Gly Gly Gln Lys Tyr Lys
            290                 295                 300

Ser Pro Lys Asn Ala Tyr Val Glu Gly Asp Ala Ser Ser Ala Ser Tyr
305                 310                 315                 320

Phe Leu Ala Gly Ala Ala Ile Thr Gly Gly Thr Val Thr Val Glu Gly
                325                 330                 335

Cys Gly Thr Thr Ser Leu Gln Gly Asp Val Lys Phe Ala Glu Val Leu
            340                 345                 350

Glu Met Met Gly Ala Lys Val Thr Trp Thr Glu Thr Ser Val Thr Val
            355                 360                 365

-continued

```
Thr Gly Pro Pro Arg Glu Pro Phe Gly Arg Lys His Leu Lys Ala Ile
    370             375             380

Asp Val Asn Met Asn Lys Met Pro Asp Val Ala Met Thr Leu Ala Val
385             390             395                     400

Val Ala Leu Phe Ala Asp Gly Pro Thr Ala Ile Arg Asp Val Ala Ser
            405             410             415

Trp Arg Val Lys Glu Thr Glu Arg Met Val Ala Ile Arg Thr Glu Leu
            420             425             430

Thr Lys Leu Gly Ala Ser Val Glu Glu Gly Pro Asp Tyr Cys Ile Ile
        435             440             445

Thr Pro Pro Glu Lys Leu Asn Val Thr Ala Ile Asp Thr Tyr Asp Asp
    450             455             460

His Arg Met Ala Met Ala Phe Ser Leu Ala Ala Cys Ala Glu Val Pro
465             470             475                     480

Val Thr Ile Arg Asp Pro Gly Cys Thr Arg Lys Thr Phe Pro Asp Tyr
            485             490             495

Phe Asp Val Leu Ser Thr Phe Val Lys Asn
            500             505
```